United States Patent
Farbood et al.

(12)

(10) Patent No.: US 6,187,741 B1
(45) Date of Patent: Feb. 13, 2001

(54) PROCESS FOR PREPARING SATURATED LACTONES, PRODUCTS PRODUCED THEREFROM AND ORGANOLEPTIC USES OF SAID PRODUCTS

(75) Inventors: Mohamad I. Farbood, Holmdel; Laura E. Kizer, Sea Bright; James Morris, Freehold; Gail Harris, Aberdeen; Lynda B. McLean, Matawan, all of NJ (US)

(73) Assignee: International Flavors & Fragrances Inc., New York, NY (US)

( * ) Notice: Under 35 U.S.C. 154(b), the term of this patent shall be extended for 0 days.

(21) Appl. No.: 09/411,830

(22) Filed: Oct. 4, 1999

Related U.S. Application Data

(62) Division of application No. 09/064,742, filed on Apr. 23, 1998, now Pat. No. 6,117,835.

(51) Int. Cl.[7] ............... A61K 7/46; C12N 1/16; C12P 17/06; C12P 7/62; C12P 7/24

(52) U.S. Cl. ............... 512/25; 512/11; 512/26; 435/255; 435/125; 435/135; 435/147; 435/911; 426/650

(58) Field of Search ............ 435/255, 125, 435/135, 147, 911; 426/650; 512/11, 25, 26

(56) References Cited

U.S. PATENT DOCUMENTS

| 5,128,261 | * | 7/1992 | Maria de Laat et al. | 435/255 |
| 5,763,233 | * | 6/1998 | Gocho et al. | 435/125 |
| 5,849,551 | * | 12/1998 | Kümin et al. | 435/126 |

FOREIGN PATENT DOCUMENTS

| 4401388A1 | * | 7/1995 | (DE) . |
| 0952226A1 | * | 10/1999 | (EP) . |
| 09182598A | * | 7/1997 | (JP) . |

* cited by examiner

*Primary Examiner*—Jill Warden
*Assistant Examiner*—Monique T. Cole
(74) *Attorney, Agent, or Firm*—Arthur L. Liberman

(57) ABSTRACT

A two phase environmentally friendly fermentation process for producing high yields of δ-decalactone and δ-dodecalactone from the corresponding unsaturated starting materials is carried out under oxidative growth conditions using a saccharomyces species. The resulting products impart, augment and/or enhance the aroma and/or taste of consumable materials including foodstuffs, chewing gums, toothpastes, beverages, fragrance compositions, colognes and perfumed articles such as solid or liquid, anionic, cationic, non-ionic or zwitterionic detergents, fabric softeners, and hair preparations.

20 Claims, 16 Drawing Sheets

GLC. PROFILE FOR EXAMPLE I.

GLC. PROFILE FOR EXAMPLE I.

GLC PROFILE FOR EXAMPLE II.

GLC PROFILE FOR EXAMPLE III.

GLC PROFILE FOR EXAMPLE IV.

GLC PROFILE FOR EXAMPLE V.

GLC PROFILE FOR EXAMPLE VI.

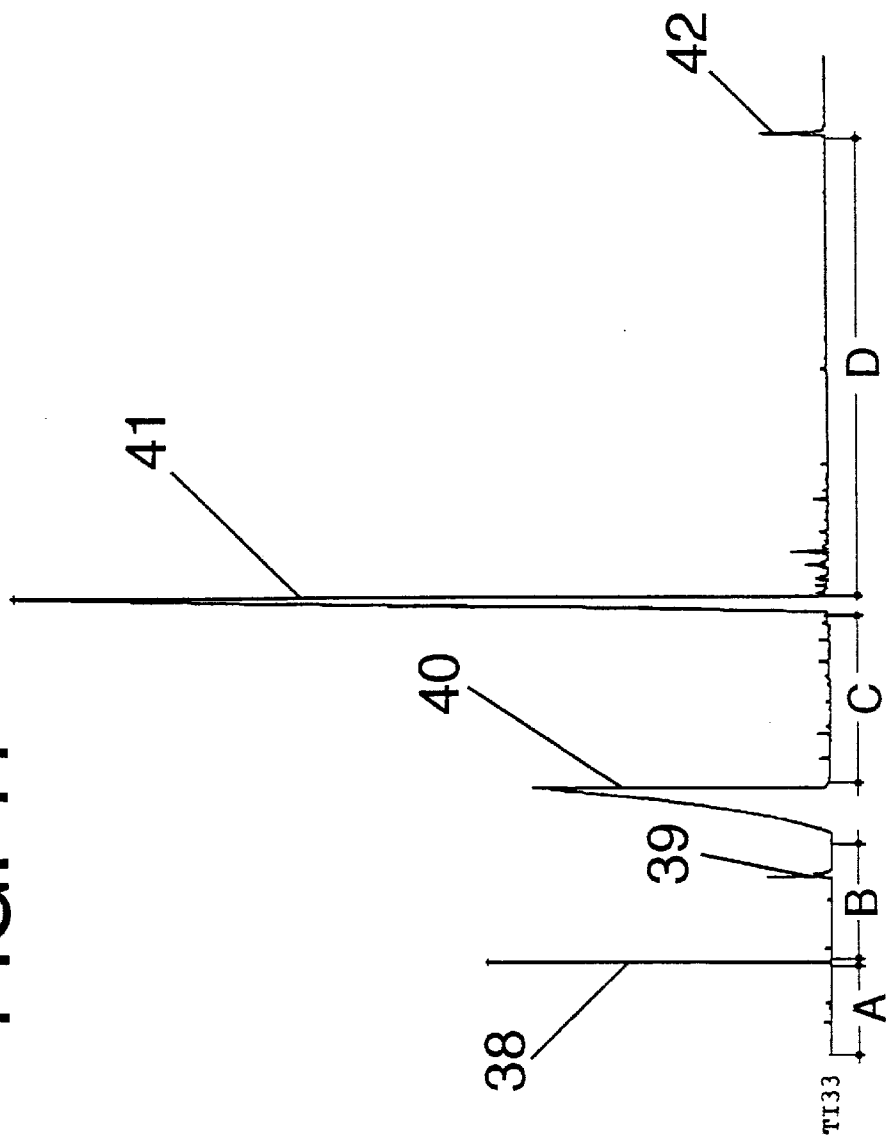

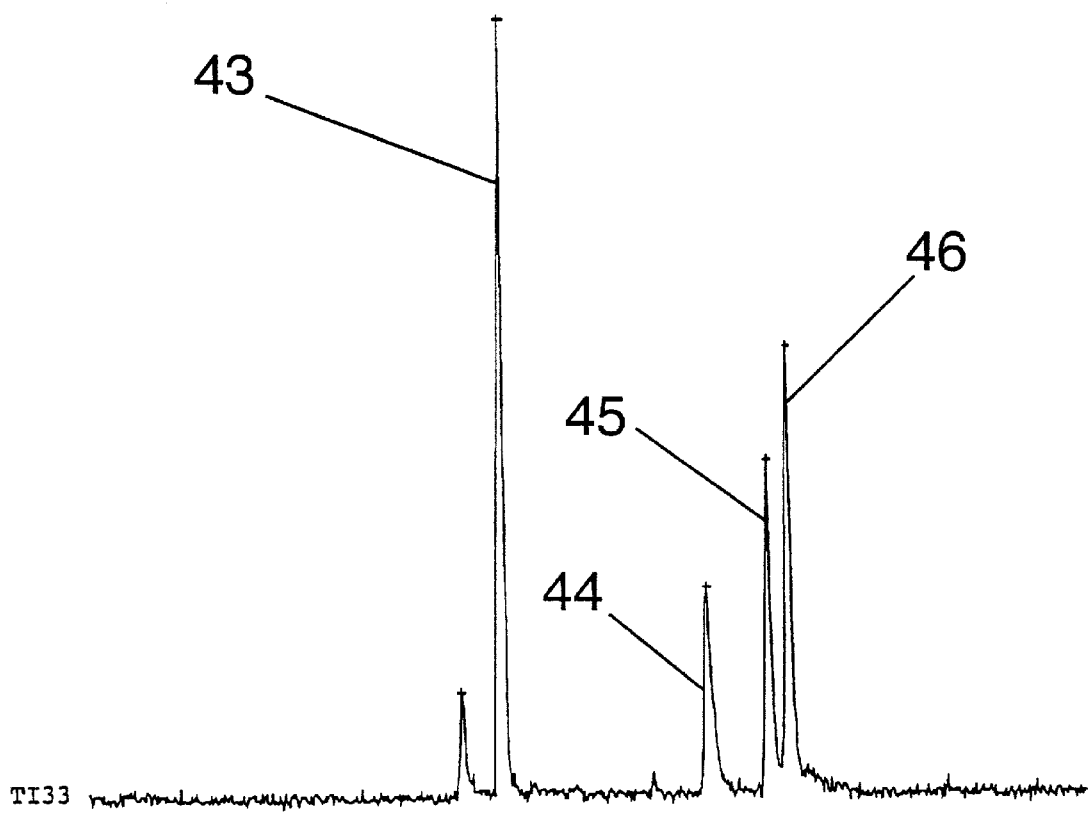
FIG. 11-A

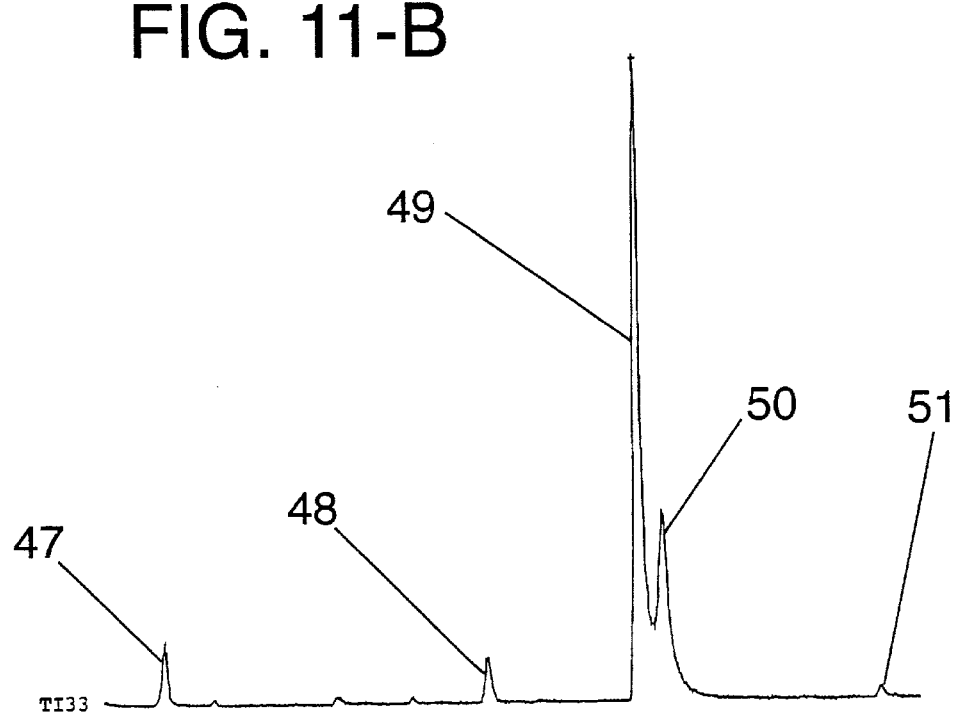
FIG. 11-B

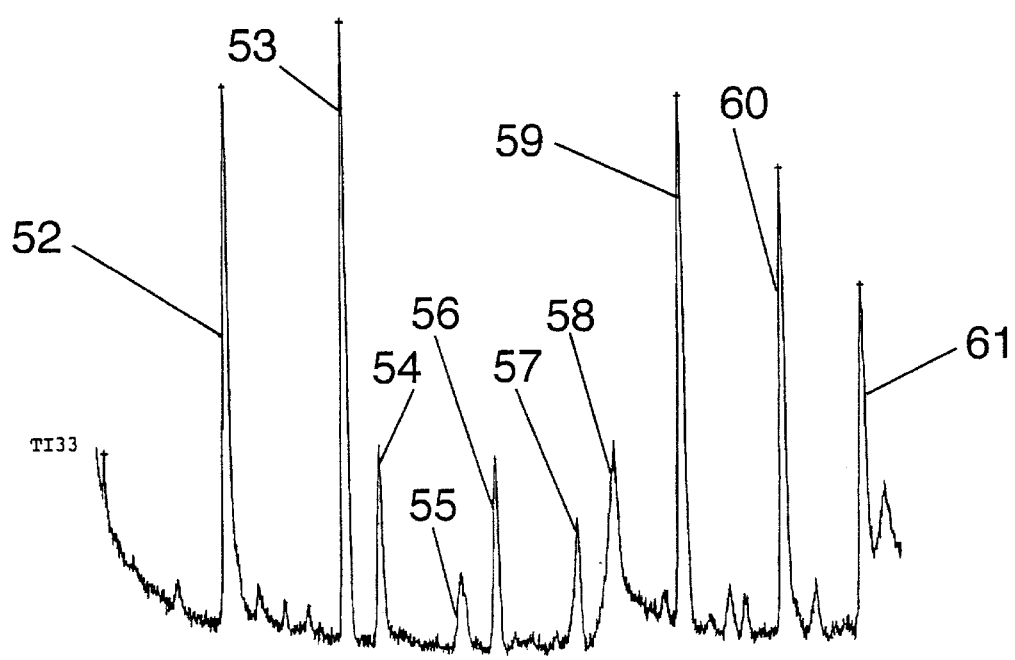
FIG. 11-C

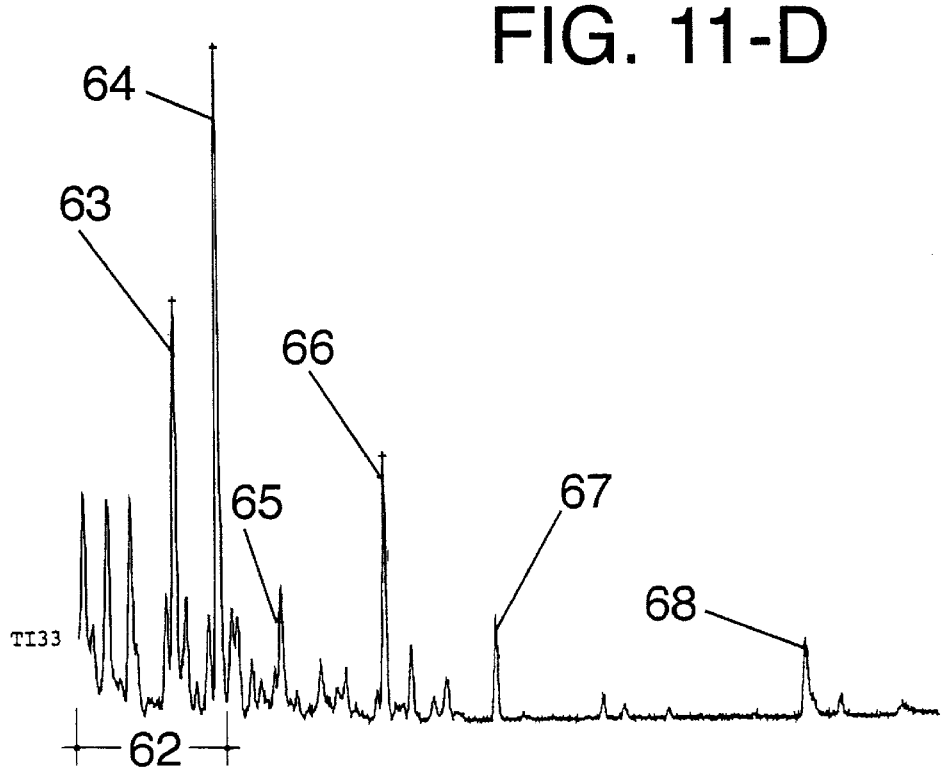
FIG. 11-D

PROCESS FOR PREPARING SATURATED LACTONES, PRODUCTS PRODUCED THEREFROM AND ORGANOLEPTIC USES OF SAID PRODUCTS

This is a divisional of application Ser. No. 09/064,742 filed on Apr. 23, 1998 now U.S. Pat. No. 6,117,835 issued on Sep. 12, 2000.

The present invention relates to a two phase microbial process for the preparation of compositions containing certain saturated lactones. In a further aspect, the present invention relates to products produced by the microbial process.

In a still further aspect, the present invention relates to organoleptic uses of said products.

In today's market, it is frequently desirable to identify flavor components of food items as being "natural flavors". It is generally recognized in the industry that a flavor compound having been prepared by microbial processes can be designated as a natural product and therefore have an important place in the commercialization of products containing them. As a result, the industry has devoted considerable time and effort to develop methods for the production of flavoring components and, in particular, for the production of lactones which can be called "natural".

Thus, as an example of such prior developments a method for preparing certain optically active delta lactones and the corresponding hydroxy carboxylic acids by microbial reduction of ketocarboxylic acids is shown in U.S. Pat. No. 3,076,750.

Investigations reported in the *Journal of Biochemistry*, 54, pages 536–540 (1963) relate to metabolism of ricinoleic acid by some Candida strains and show that gamma hydroxydecanoic acid is an intermediate in the oxidative degradation of ricinoleic acid. In a number of such prior disclosed methods, the processes were not entirely satisfactory because of the toxicity of certain components to the microorganism.

A method of producing optically active gamma hydroxydecanoic acid by culturing or incubating a microorganism capable of hydrolyzing castor oil and effecting beta oxidation of the resulting hydrolysate in the presence of castor oil to produce gamma hydroxydecanoic acid is shown in U.S. Pat. No. 4,560,656.

This reference also discloses a method of producing optically active gamma hydroxydecanoic acid by enzymatically hydrolyzing castor oil using lipase to form an enzymatic hydrolyzate and culturing a microorganism capable of effective beta-oxidation of the enzymatic hydrolyzate in the presence of the hydrolyzate to produce gamma hydroxydecanoic acid. Similarly, a way of culturing or incubating the microorganism capable of hydrolyzing castor oil and a microorganism capable of affecting beta oxidation of the castor oil hydrolyzate in the presence of the castor oil to produce gamma hydroxydecanoic acid is also shown in that document.

European published patent application 258993 of Apr. 9, 1988 discloses a process for the production of optically active gamma hydroxydecanoic acid suitable for conversion to optically active gamma decalactone.

Microbial production of natural δ-dodecalactone from Massoi bark oil was discussed by van der Shaft et al. in *Applied Microbiology and Biotechnology* (1992) Vol. 36, pages 712–716.

The usefulness of yeast for reduction reactions in general, including conversion of Massoi lactone is referred to by N. J. Turner in *Chemistry & Industry*, Aug. 1, 1994 pages 592 et seq.

Japanese application 09 031071-A discloses production of (R)-(−)-massoi lactone by incubating a microorganism.

More recently, in U.S. Pat. No. 5,128,261, 5-decanolide and 5-dodecanolide have been shown to be produced from a series of strains of yeast in a fermentation reaction by carrying out a biocatalytic reduction of the corresponding natural unsaturated 5-olides. such prior methods are said to be economically attractive but there is a constant need for improvement of yields and conversion which is addressed in this invention.

In the flavor and fragrance art the need has risen for the development of more efficient production of naturally occurring lactones which have heretofore been found to be useful and necessary in the creation of flavor formulation used in augmenting or enhancing the aroma or taste of such items as foodstuffs, chewing gums and toothpastes, and also useful in augmenting or enhancing the aroma of perfume compositions such as colognes, perfumed articles either in solid or liquid state as, for example, ionic, cationic, nonionic or zwitterionic detergents, perfumed polymers, fabric softener compositions, fabric softener articles, hair preparations and cosmetic powders.

It is therefore an object of the present invention to provide a new and improved method for preparing certain saturated naturally occurring lactones found to be suitable for a wide variety of purposes in a more efficient manner to produce a higher yield and greater conversion.

SUMMARY OF THE INVENTION

The above and other objects and features of the invention are obtained in accordance in the present invention by carrying out a process using oxidative reaction techniques to produce and recover certain naturally occurring saturated lactones found to be useful for their organoleptic properties in augmenting or enhancing the aroma or taste of consumable materials such as foodstuffs, chewing gums, toothpaste, additional products, chewing tobaccos, smoking tobaccos, perfume compositions, colognes and perfumed articles such as solid or liquid detergents, perfumed polymers, fabric softener compositions, fabric softener articles, cosmetic powders, hair preparations and the like, which saturated lactones are defined according to the structure:

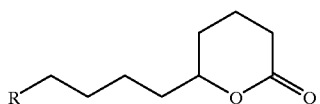

I wherein R is a member selected from the group consisting of methyl and n-propyl. These compounds are δ-decalactone and δ-dodecalactone, respectively.

The process to produce the lactone compositions of the invention are carried out under oxidative growth conditions by preparing (1) an aqueous nutrient medium including a source of sugar in a first aqueous liquid phase, and (2) a second non-aqueous, organic liquid phase (which is the "organic" phase) containing a significant concentration of the unsaturated 5-olide compound represented by the structural formula:

II

[structure: R—(CH2)3—6-membered lactone ring with double bond]

wherein R is a member selected from a group consisting of methyl and n-propyl. The starting materials thus can be a natural 2-decen-1,5-olide or a natural 2-dodecen-1,5-olide compound.

The first aqueous liquid phase and the second organic liquid phase are mixed together with agitation to form a two-phase system while (i) maintaining sufficiently low dextrose levels and (ii) aerating with an oxygen-containing gas such as air or oxygen, whereby oxidative growth is achieved with surprisingly high conversion of the unsaturated 5-olide compound into the corresponding saturated 5-olide compound. The reaction is carried out in the presence of a selected yeast capable of producing the natural δ-lactone.

A further feature of the present invention resides in the products produced by the present invention characterized by the GLC profiles which accompany this application.

Still further, another feature of the invention resides in the flavor and fragrance compositions containing the δ-decalactone and δ-dodecalactone products produced by the present invention.

BRIEF DESCRIPTION OF THE DRAWINGS

The present invention will be further understood with reference to the accompanying drawings wherein.

[CH3—(CH2)4—δ-lactone structure]

Figure 2:
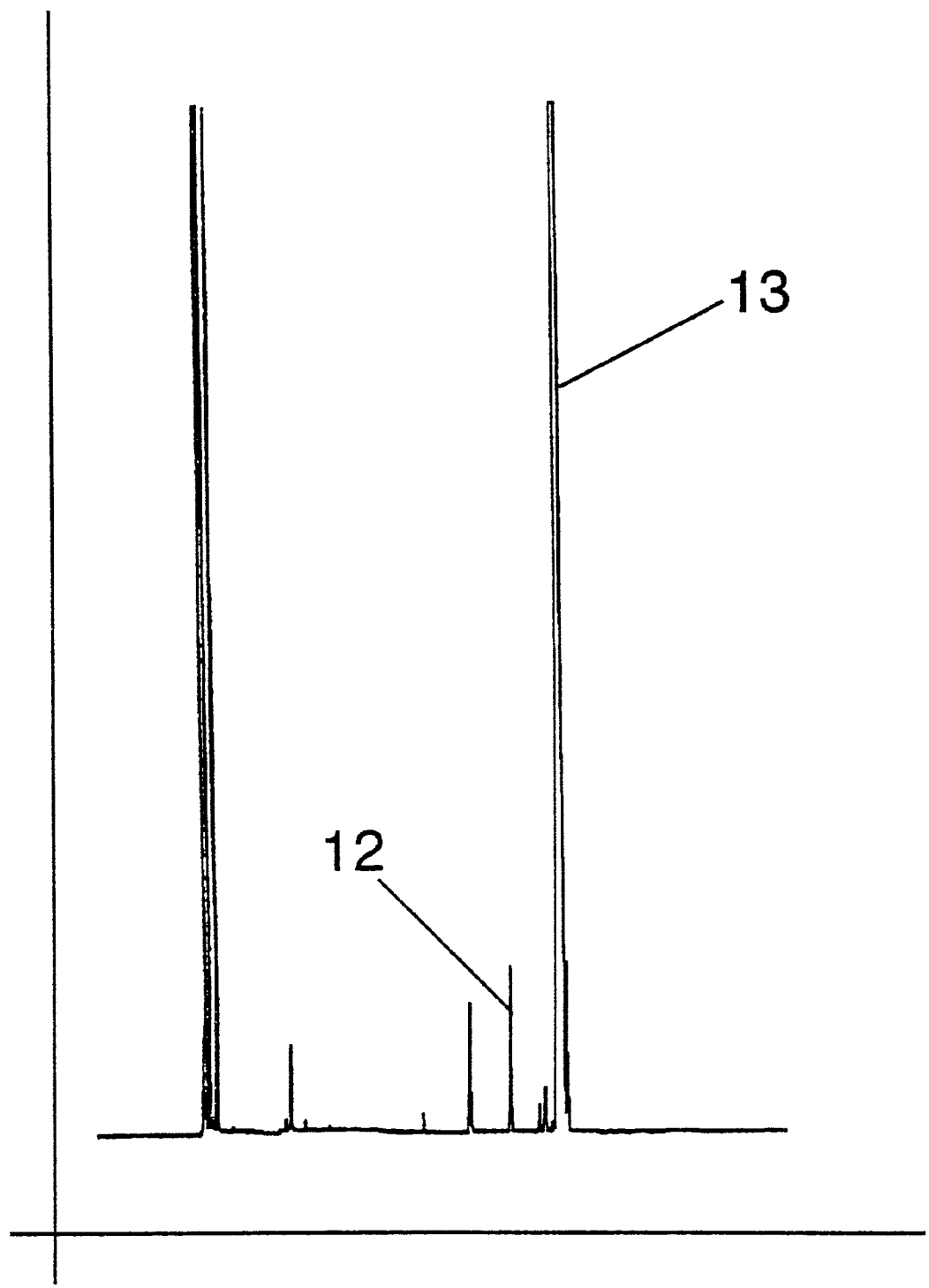

FIG. 2 is a GLC profile for the reaction product of example 2 containing the compound having the structure:

[CH3—(CH2)4—δ-lactone structure]

Figure 3:
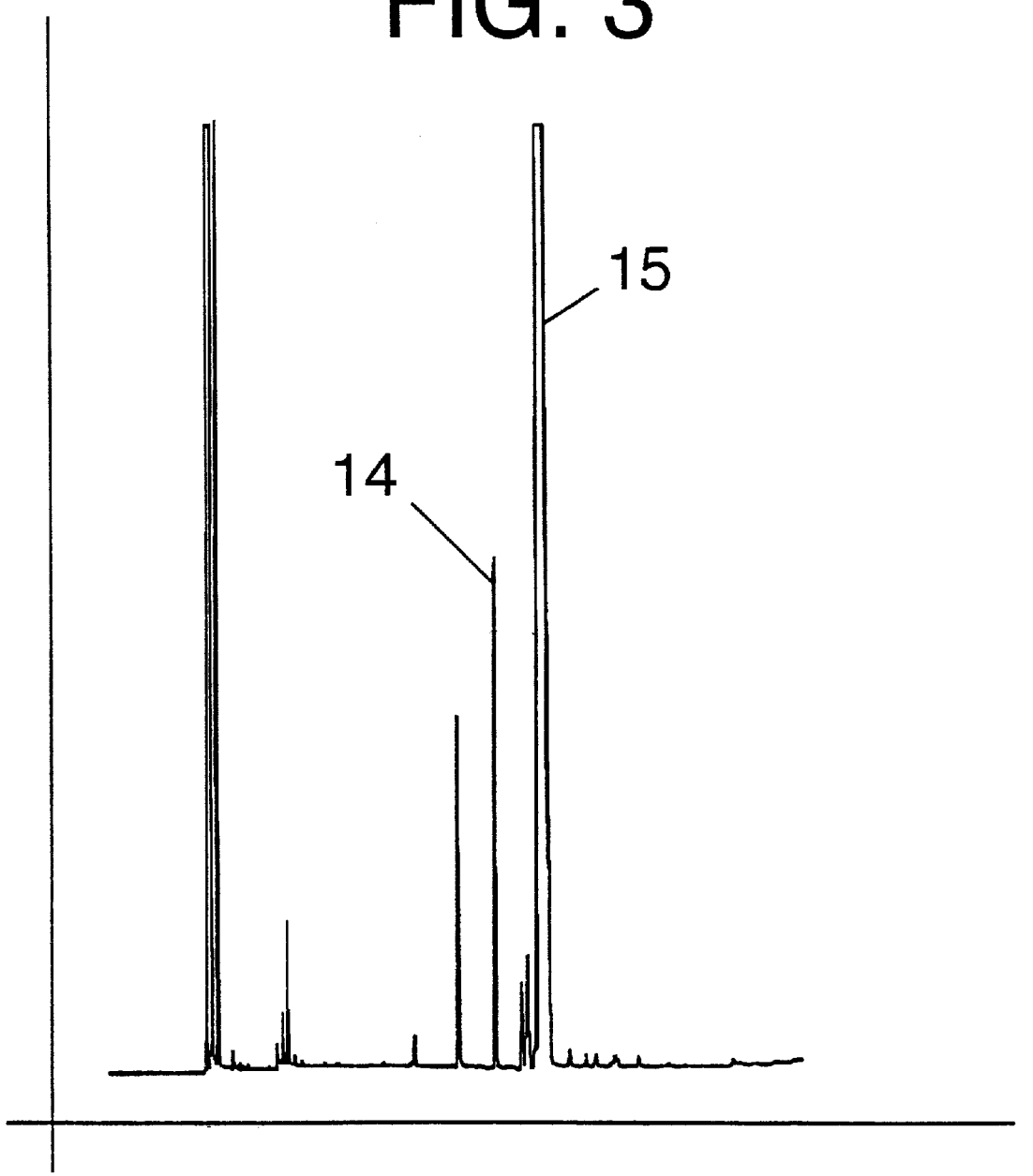

FIG. 3 is a GLC profile for the reaction product of example 3 containing the compound having the structure:

[CH3—(CH2)4—δ-lactone structure]

Figure 4:
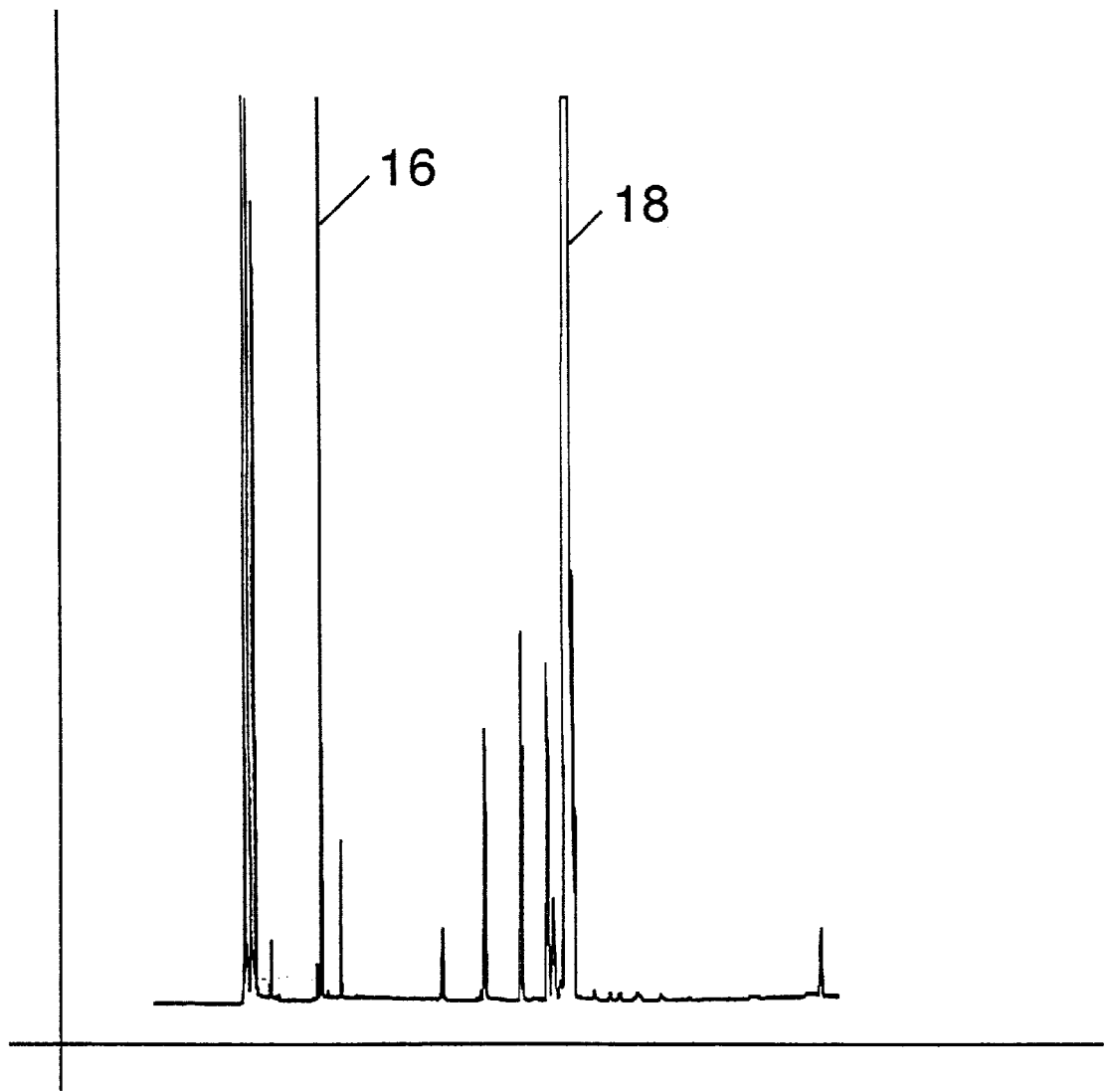

FIG. 4 is a GLC profile of the reaction product of example 4 containing the compound having the structure:

[CH3—(CH2)4—δ-lactone structure]

Figure 5:
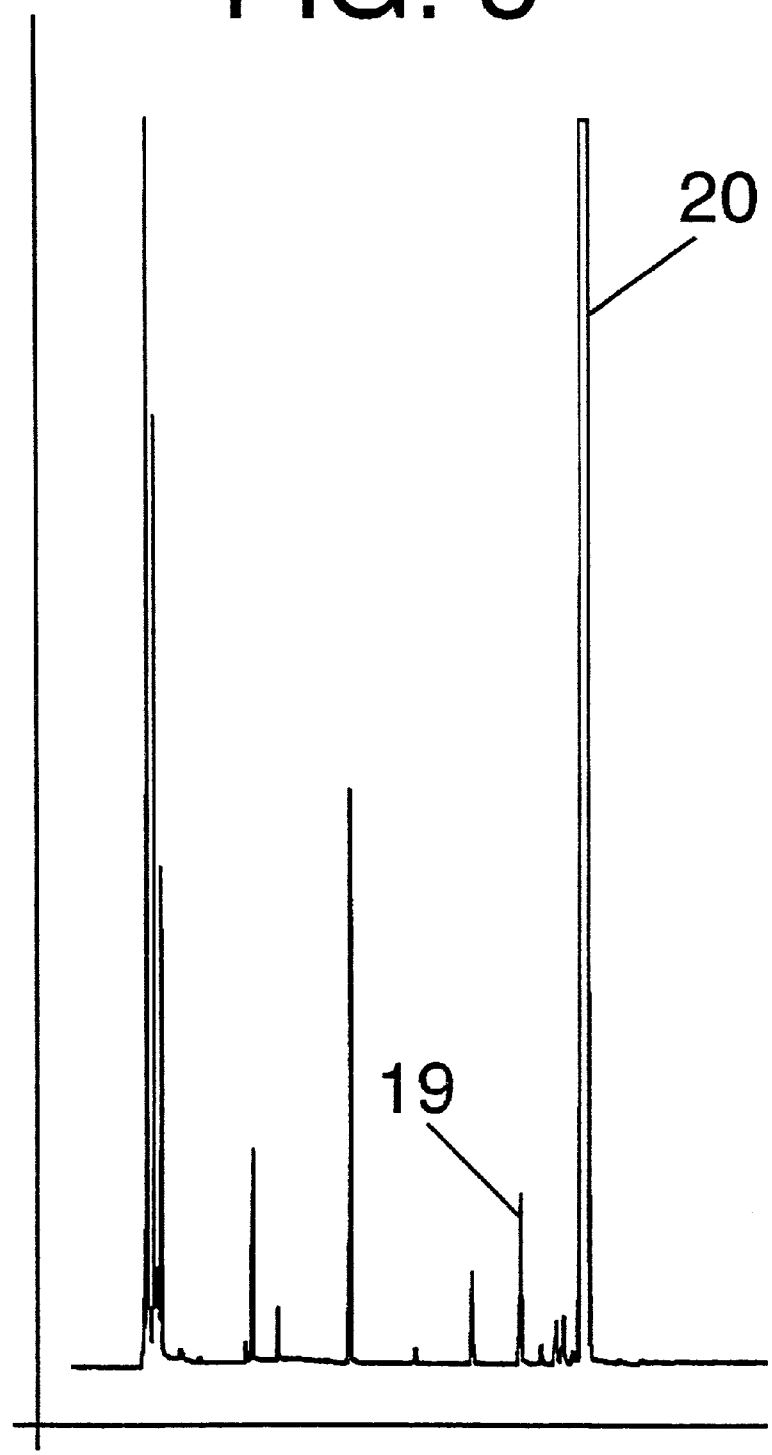

FIG. 5 is a GLC profile for the reaction product of example 5 containing the compound having the structure:

[CH3—(CH2)4—δ-lactone structure]

Figure 6:
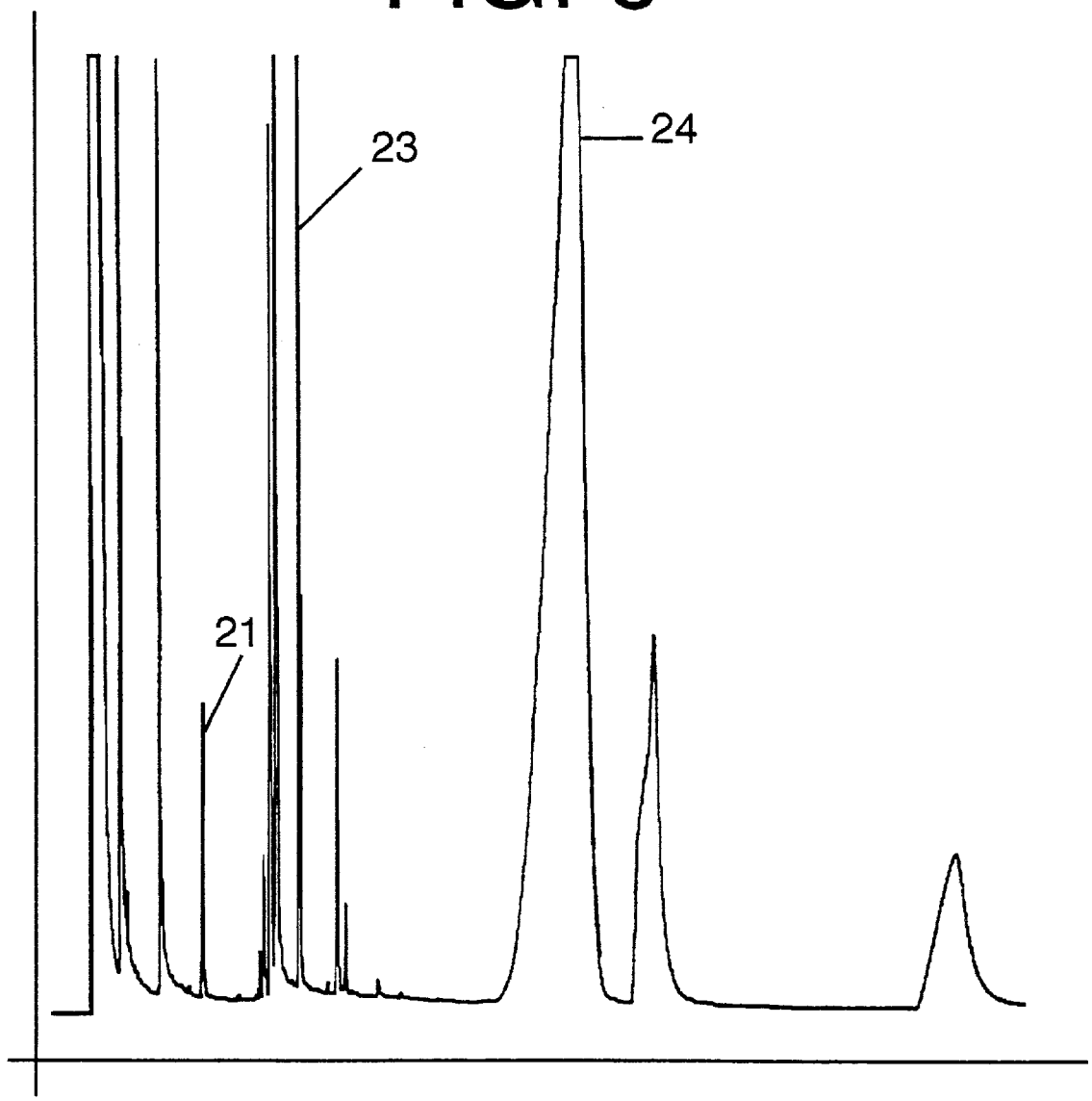

FIG. 6 is a GLC profile for the reaction product of example 6 containing the compound having the structure:

[CH3—CH2—CH2—(CH2)4—δ-lactone structure]

Figure 7:
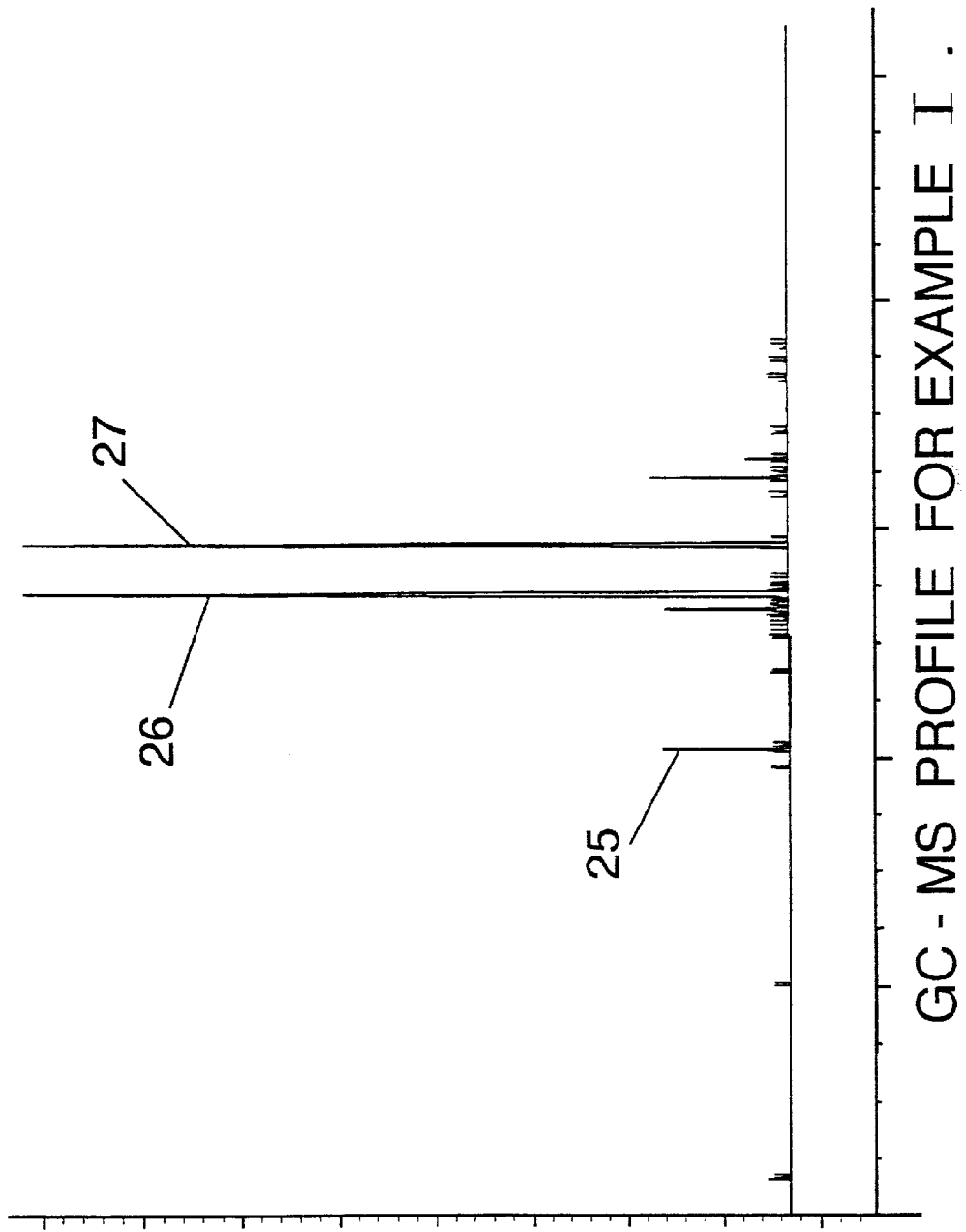

FIG. 7 is a mass spectrum for the starting material Massoi bark oil used as a starting material in example 1.

Figure 8:
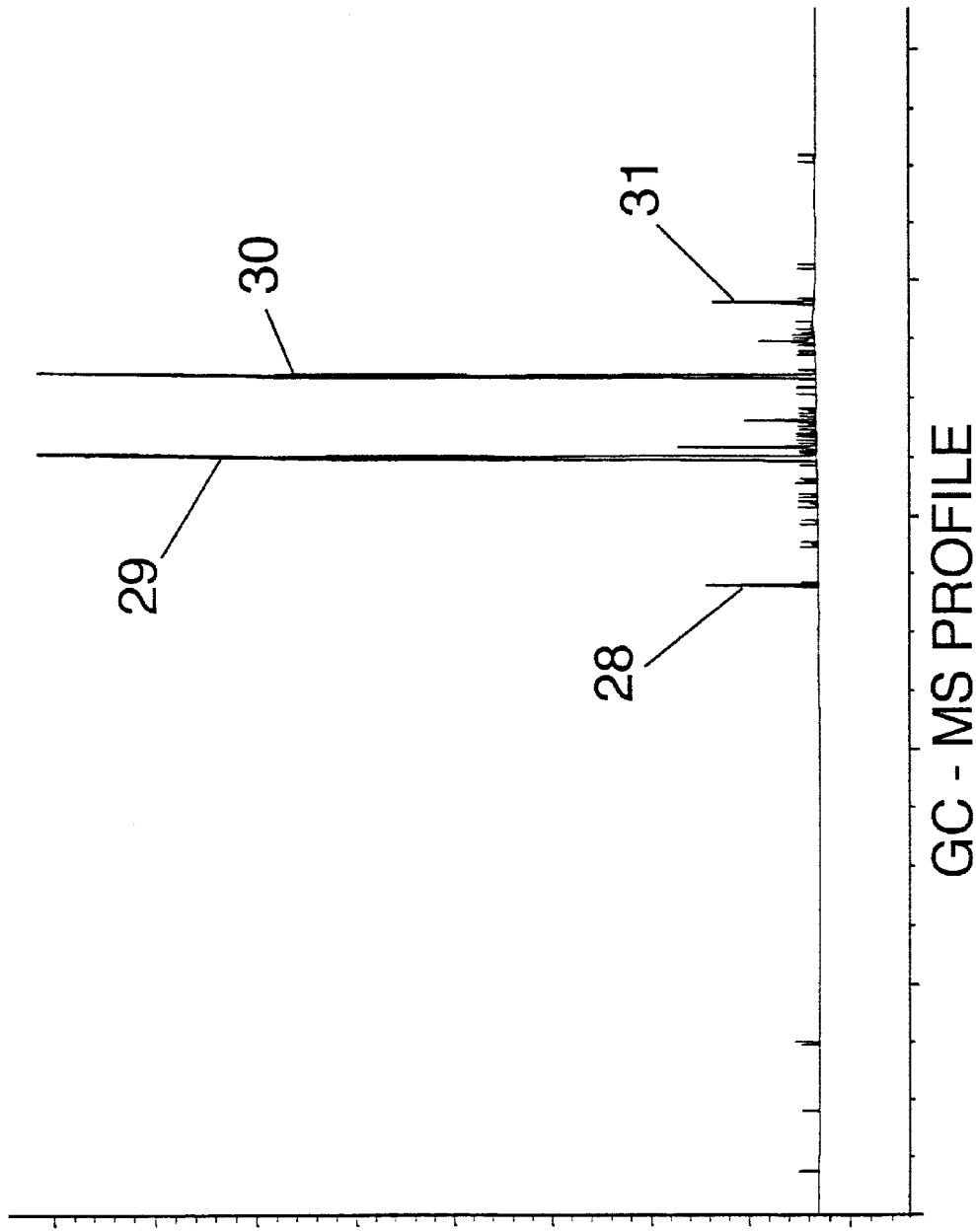
Figure 9:
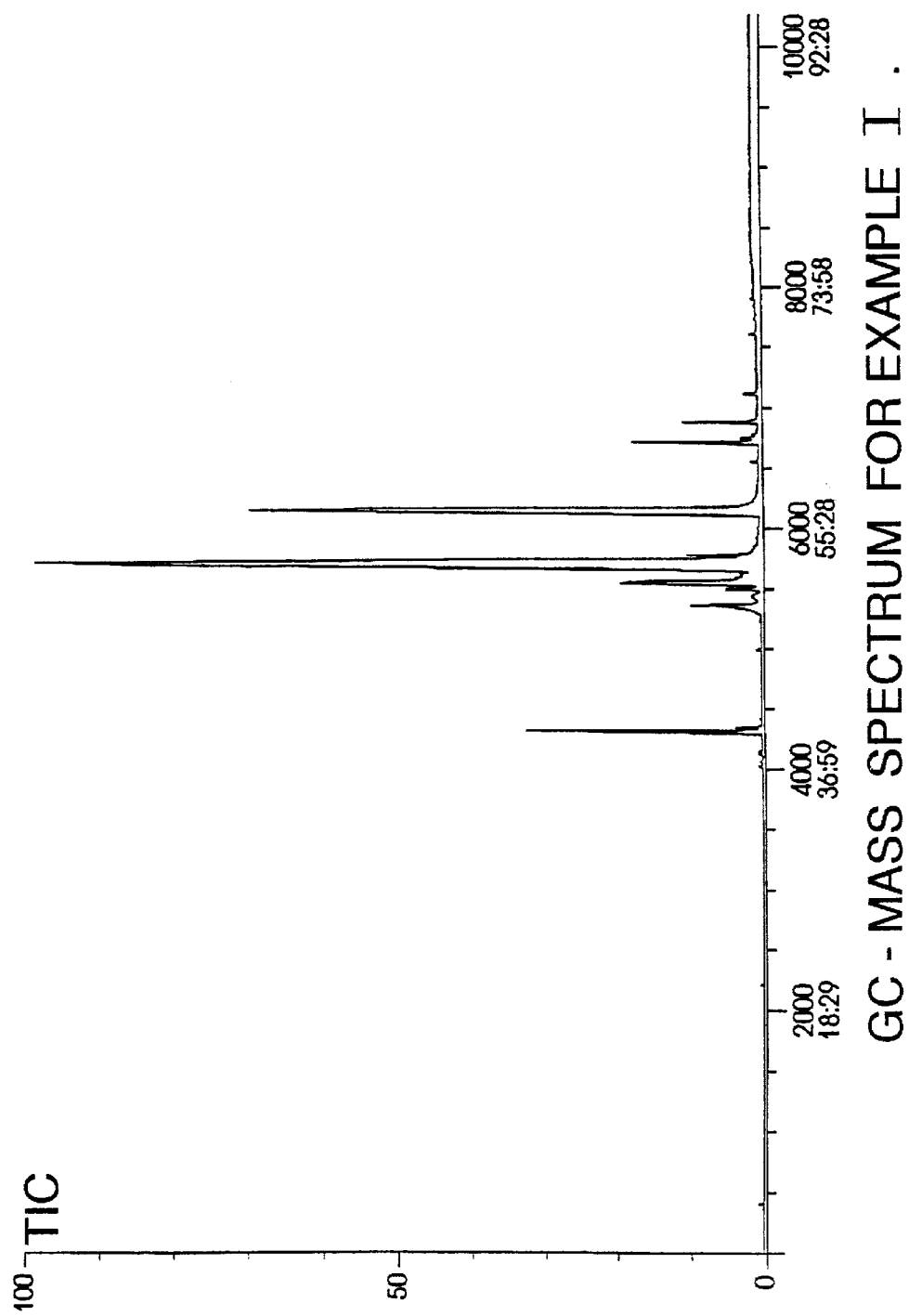
Figure 10:
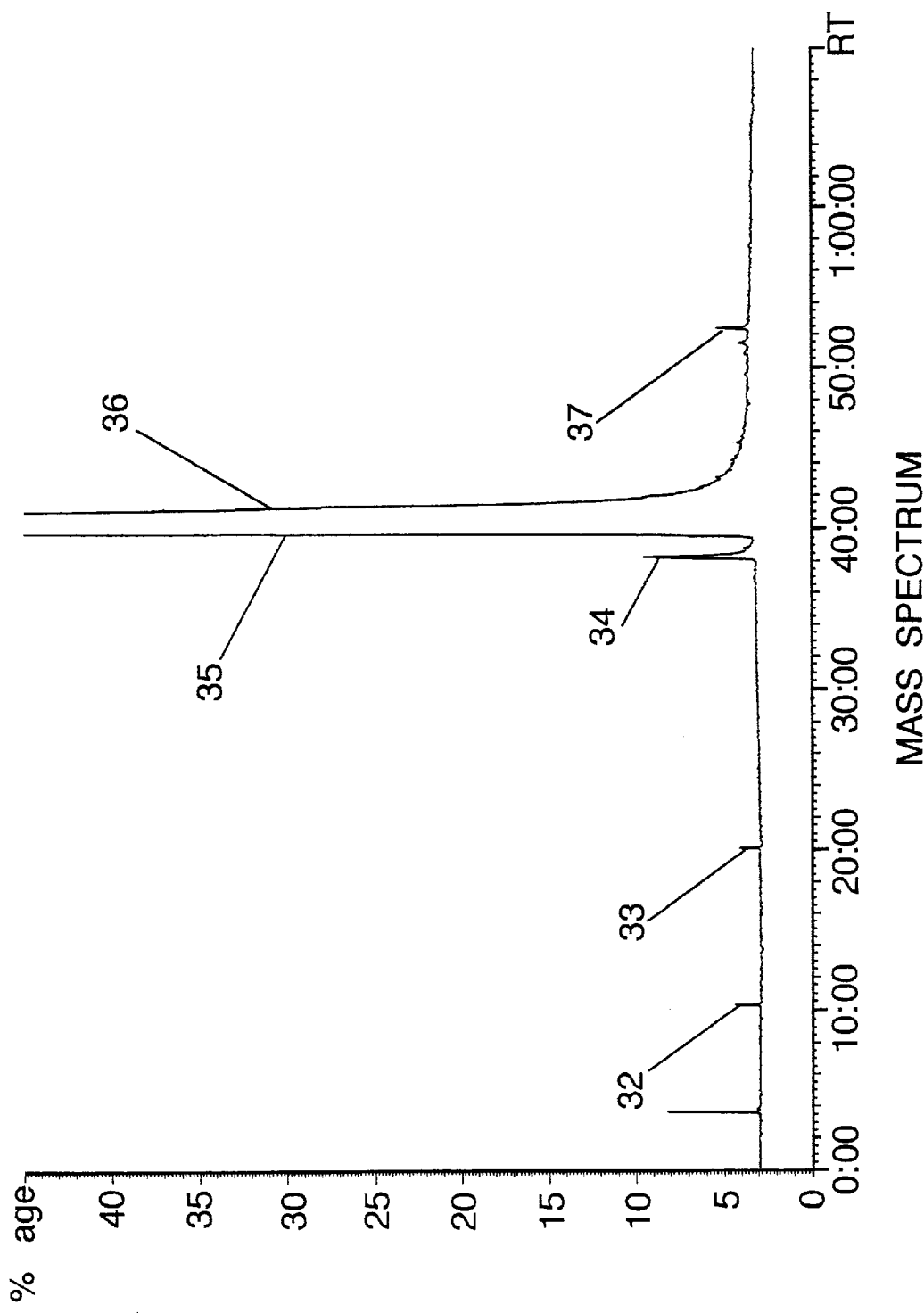

FIG. 8 is a mass spectrum for the starting material Mauri bark oil used as a starting material according to the invention;

FIG. 9 is a mass spectrum for the starting material used in example 1;

FIG. 10 is a mass spectrum for the starting material containing some of the lactone product (0.93%);

FIG. 11 is a mass spectrum total ion chromatogram (TIC) of the distillation fraction 2 of Example 1;

FIG. 11A is an expanded TIC of section A shown in FIG. 11;

FIG. 11B is an expanded TIC of section B shown in FIG. 11;

FIG. 11C is an expanded TIC of section C shown in FIG. 11;

FIG. 11D is an expanded TIC of section D shown in FIG. 11; and

Figure 12:
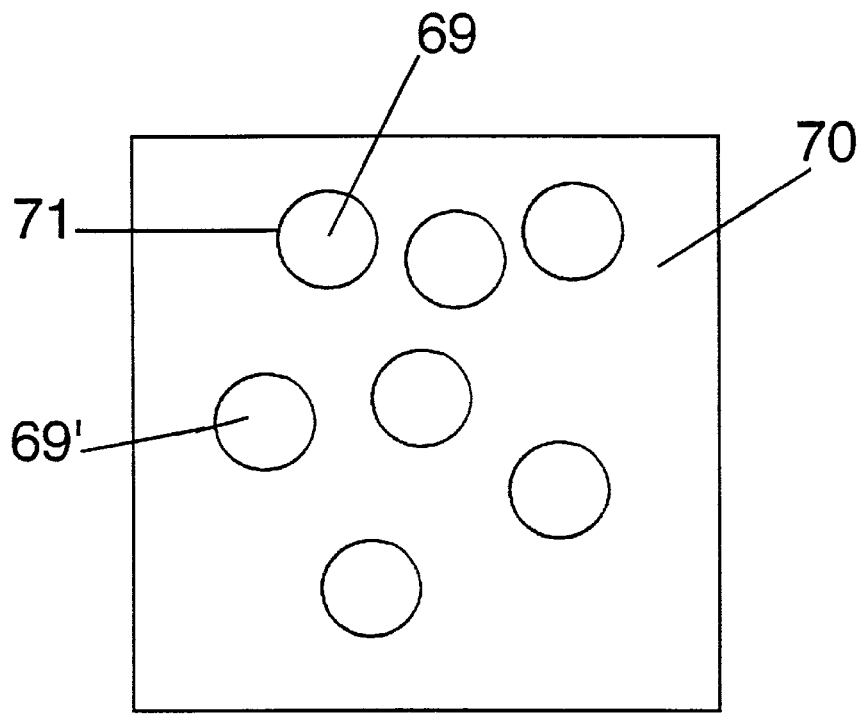

FIG. 12 is a schematic view of reaction system according to the present invention.

DETAILED DESCRIPTION OF INVENTION

The reaction according to the present invention is shown thusly:

[R—(CH2)3—unsaturated δ-lactone → R—(CH2)3—saturated δ-lactone]

wherein R is methyl or n-propyl.

More specifically, the reaction involving oxidative growth concerns (i) maintenance of sufficiently low dextrose levels in the reaction medium and (ii) the use of an oxygen containing gas such as air or oxygen which is dissolved in a L relatively high amount into the reaction medium. In the process of the invention the yeast species that is preferably used is Saccharomyces cerevisiae. However, other yeast species of Saccharomyces can be used to obtain comparable results.

The process is carried out by first introducing an inoculum of the selected yeast species into a reaction vessel which contains a production medium, typically including glycine or other equivalent nutrient source, a buffering agent such as $KH_2PO_4$, a yeast extract and other nutrient sources which may include trace minerals and growth factors.

Immediately subsequent to the introduction of the inoculum, a source of dextrose in a suitable nutrient medium is begun feeding into the reaction vessel (and throughout the entire fermentation procedure).

Up to about 30 hours after inoculation, a mixture of the unsaturated clide compound; namely 2-decen-1,5-olide or 2-dodecen-2,5-olide and a fatty acid ester (the organic phase) (or substitute therefor as set forth infra) is-pumped into the reaction vessel.

A particularly suitable fatty acid ester is NEOBEE® oil which is a triglyceride of $C_8$–$C_{10}$ fatty acids. Other suitable fatty acid esters can be used for this purpose for example olive oil, castor oil, safflower oil, soybeam oil and the like. In place of the triglycerides, high molecular weight hydrocarbons such as hexadecane and tetradecane can be used. The mixture of the unsaturated olide compound and the fatty acid ester (or substitute therefor) constitutes the second liquid organic phase. The triglyceride (or substitute therefore) functions, inter alia, as the organic phase former and keeps the substrate separated from the yeast.

It must be emphasized that the product and substrate are each toxic to the microorganism, Saccharomyces. Accordingly, our novel two phase process gives rise to a diminution of such toxicity thus resulting in a surprisingly substantial increase in product yield and conversion. Such diminution of toxicity is created by the low partition coefficient between the two phases: the organic phase containing relatively high concentrations of olide reactant and product and the aqueous phase containing the microorganism, the actual reaction taking place proximate the phase interface.

Furthermore, our novel two phase fermentation surprisingly reduces the cost of product recovery. The organic-phase-containing product is easily separable from the aqueous phase by a simple procedure, i.e. the use of a centrifuge or other simple phase separation techniques. The product is recovered from the organic phase by means of routine distillation, and the triglyceride (or substitute therefor) is recycled thus giving rise to an environmental advantage. Our approach eliminates the high cost of extraction using an environmentally unacceptable organic solvent and substantially eliminates all environmental safety issues, and health hazards that are associated with the use of such environmentally unacceptable organic solvents.

The nutrient feed which contains the dextrose and may also contain a solution of vitamins as desired and trace mineral solutions as desired as well as buffers, and the like is pumped into the reaction vessel.

It is to be understood that the production medium and the nutrient medium suitable for the present invention are well known and understood by persons skilled in the art.

The fermentation reaction is permitted to proceed being careful to maintain oxidative growth conditions in the reaction vessel by balancing dextrose feed and oxygen injection into the system. Thus, the concentration of the dextrose is maintained at least about 0.01 grams per liter to as much as 1.5 grams per liter, preferably 0.1 to 0.5 grams per liter, most preferably at about 0.03–0.07 grams per liter during the fermentation reaction. The preferred operable range of dextrose concentrations during the fermentation is a function of the specific Saccharomyces organism species or strain used. The actual dextrose concentration varies at any given time from a minimum to a maximum recognizing that too high a dextrose concentration will result in fermentative growth and production of ethyl alcohol resulting in lower biomass production (giving rise to much lower product yield and conversion). By automatic addition of the nutrient feed, the nutrient feed rate can range from about 5 to about 72 grams per liter per hour.

The desired temperature of the reaction is approximately 30° C. although this can vary as will be understood by persons skilled in this art. The optimum temperature of the reaction can be readily determined by skilled operators using parameters well understood in the fermentation art. A typical range of temperature is 20 to 50° C. It is a feature of the fermentation reaction of the present invention to avoid the formation of excessive amounts of alcohol which is typically produced in prior known methods. Under the reaction conditions discovered by applicants, unwanted alcohol production is avoided by a control of the dextrose addition and charging of the oxygen source to the system. Thus, the rate of dextrose addition and oxygen (or air) addition is such, -as to maintain oxidative growth in the reaction medium, avoiding the formation of excessive $C_2H_5OH$, and enabling the substrate; namely, the unsaturated olide compound to slowly diffuse out of the organic phase into the aqueous phase and thereby control the reaction to form the saturated olide compound product as discussed supra.

As an example of oxygen in the system, the oxygen is introduced at a rate which is at least about 0.1 liters per liter of reaction mixture. The injection of air or other oxygen containing gas is controlled so as to measure at least 10% dissolved oxygen as measured by a standard oxygen probe at all times during the reaction.

The resulting products in the form of mixtures of saturated lactones or as separate lactones or groups of lactones are useful in augmenting or enhancing the aroma or taste of consumable materials as set forth herein.

The form in which the microorganism Saccharomyces yeast is used is not critical. It can be used as a culture in a suspension including the cells and the corresponding nutrient solution or in the form of cells suspended in a buffering solution. The cells or an enzyme extract thereof may be immobilized on a suitable solid support which may then be used to effect the transformation.

The culture suspension is prepared by inoculation of a suitable medium with the microorganism. A suitable medium is one which contains carbon sources, nitrogen sources, inorganic salts and growth factors. Among the suitable carbon sources are for example, glucose, galactose, L-sorbose, maltose, sucrose, cellobiose, trehalose, L-arabinose, L-rhamnose, ethanol, glycerol, L-erythritol, D-mannitol, lactose, melibiose, raffinose, melezitose, starch, D-xylose, D-sorbitol, alpha-methyl-D-glucoside, lactic acid, citric acid and succinic acid. Among the suitable nitrogen sources are, for example, nitrogen containing organic substances such as peptone, meat extract, yeast extract, corn steep liquor, casein, urea, amino acids, or nitrogen containing inorganic compounds such as nitrates, nitrites, and inorganic ammonium salts. Among the suitable inorganic salts are, for example, phosphates of magnesium, potassium, calcium, and sodium. The above mentioned nutrients in the culture medium may be supplemented with, for example, one or more vitamins of the B Group and/or one of more trace minerals such as Fe, Mo, Cu, Mn, B as desired. However, the process can be performed in a vitamin-free medium; for example, when a small amount of yeast extract is added to the medium there is no need for vitamins or trace minerals.

The cultivation of the microorganism can be carried out as a stationary culture or as a submerged culture (e.g. shaking culture, fermentors) preferably under aerobic conditions. One suitably may work in the pH range of from about 3.5 to about 8.0, and preferably in the range of from about 4.0 to about 7.5. The pH may be regulated by the addition of inorganic or organic bases, such as aqueous or gaseous ammonia, sodium hydroxide, potassium hydroxide, calcium hydroxide, calcium carbonate, by ion-exchange resins, or by the addition of a buffer such as phosphate or phthalate. The incubation temperature is suitably maintained at between about 15° C. and about 33° C., with a range from about 20° C. to about 30° C. being preferred.

The process in accordance with the invention is conveniently carried out by adding a source of sugar, such as dextrose to the culture medium at the onset of cultivation, as the carbon source. Alternatively, the dextrose may be added in combination with another carbon source, as mentioned above, either during cultivation, or when the cultivation is complete. The amount level, or concentration of the substrate in the medium may vary. For example, in the case of sources of dextrose, levels of from about 0.3% to about 5% may make up the medium initially or be added during the course of the oxidative growth, although the specific level of dextrose source may be easily determined and can be varied.

The reaction time may vary depending on the composition of the culture medium and the substrate concentration. In general, shaking flask cultures require from between about 2 h. and about 240 h. depending upon the microorganism and the composition of the culture medium. However, when a fermenter vessel is used the oxidative reduction reaction time may be reduced to about 100 h. or less.

The reaction of this invention may be carried out using the cells of the yeast microorganism isolated from the culture solution, or with an enzyme extract isolated from the cells in a manner known per se. The yeast cells may be immobilized on a solid support and the desired transformation effected in the absence of the live yeast microorganism. The transformation of the substrate may be effected by mutants of the yeast microorganism. Such mutants can be obtained readily by methods well known in the art, for example, by exposing the yeast cells to UV or X-rays, or customary mutagenic substances such as, for example, acridine orange.

The substrate which is the unsaturated olide compound is generally added directly to the production medium. Sources for the 2-decen-1,5-olide or the 2-dodecen-1,5-olide can vary but it has been found that a particularly suitable source for the purposes of this invention is Massoi bark oil and more particularly a Massoi lactone $C_{10}$ fraction for the source of 2-decen-1,5-olide. The Massoi lactone $C_{.2}$ fraction is a preferred source for the 2-dodecen-1,5-olide. Particularly suitable materials are sold by Haldin International Inc. of Closter, N.J. One such product is natural 2-decenoic delta lactone (GRAS) FEMA No. 3744 which is a pale yellow liquid with a dry musty coconut, creamy flavor and aroma with a refractive index of 1.467–1.477 and a molecular weight of 168. It is insoluble in water and soluble in alcohol with a specific gravity of 0.982–0.992.

Also available from Haldin is a natural fractionated Massoi bark oil, Fema No. 3747, which is a mixture of 2-decenoic, 2-dodecenoic and 2-tetra decenoic delta lactones. The appearance is a pale yellow liquid with a fruity, oily coconut, creamy flavor and aroma. The mixture is also insoluble in water and soluble in alcohol.

The triglyceride (or substitutes therefor) is added to the production medium with the unsaturated olide to form the organic phase. The triglyceride controls the rate of diffusion of the unsaturated clide and saturated olide product into the aqueous phase in such a way that the toxicity of substrate and product to the microorganism is substantially eliminated.

Triglycerides of $C_8$–$C_{10}$ fatty acids as well as vegetable oils and substitutes therefore cited supra are well suitable for this purpose, including the specific NEOBEE® oil.

Conventional antifoam agents, such as silicone oils (e.g., UCON®), polyalkyleneglycol derivatives, maize oil, or soya oil can be used to control foaming as is known in the art.

The saturated lactone compounds obtained in accordance with the present invention and one or more auxiliary perfume ingredients, including for example, hydrocarbons, alcohols, ketones, aldehydes, nitrites, esters, ethers, synthetic essential oils, lactones other than those of our invention, and natural essential oils may be admixed so that the combined odors of the individual components produce a pleasant and desired fragrance, particularly and preferably in the fruity area (e.g., peach and apricot aromas). Such perfume compositions usually contain (a) the main note or the "bouquet" or foundation stone of the composition; (b) modifiers which round off and accompany the main note; (c) fixatives which include odorous substances which lead a particular note to the perfume throughout all stages of evaporation and substances which retard evaporation-and (d) topnotes which are usually low-boiling, fresh-smelling materials.

In perfume compositions, it is the individual compositions which contribute to their particular olfactory characteristics, however, the overall sensory effect of the perfume composition will be at least the sum total of the effects of each of the ingredients. Thus, one or more of the lactone derivative (s) of our invention can be used to alter, modify or enhance the aroma characteristics of a perfume composition, for example, by utilizing or moderating the olfactory reaction contributed by another ingredient in the composition.

The amount of lactone derivative(s) of our invention which will be effective in perfume compositions as well as in perfumed articles and colognes depends upon many factors including the other ingredients, their amounts and the effects which are desired. It has been found that perfume compositions containing as little as 0.005% of lactone derivative(s) or even less (e.g., 0.0025) can be used to impart sweet, fresh fruity, peach aromas with sweet, creamy, nutlike topnotes and heavy fruity peach undertones to soaps, cosmetics, detergents including anionic, cationic, nonionic and zwitterionic solid or liquid detergents, perfumed polymers and other products. The amount employed can range up to 70% of the fragrance components and will depend upon the consideration of cost, nature of the end product, the effect desired on the finished product and the particular fragrance sought.

The saturated lactone compounds of this invention are useful when either taken alone or take together with other perfumery ingredients in detergents, soaps, space odorants and deodorants, perfumes, colognes, toilette waters, bath preparations, hair preparations such as lacquers, brilliantines, pomades and shampoos; cosmetic preparations such as creams, deodorants, hand lotions and sun screens; powders such as talcs, dusting powders, face powders and the like.

As little as 0.25% of the saturated lactone compound can suffice to impart intense, substantive, sweet, fresh fruity, peach aroma with sweet, creamy, and nut like topnotes and heavy fruity and peach undertones to floral and patchouli perfume formulations. Generally no more than 5% of the saturated lactone compound based on the ultimate end product is required to be used in the perfume compositions.

Furthermore, as little as 0.255 of the lactone can suffice to impart such aromas to perfumed articles per se, whether in the presence of other perfume materials or whether used by themselves. Thus, the range of use of the saturated lactone compounds of this invention in perfumed articles, e.g., perfumed polymers and solid or liquid anionic, cationic, nonionic or zwitterionic solid or liquid detergents, may vary from 0.25% up to about 5% by weight based on the total weight of the perfumed article.

In addition, the perfume composition or fragrance composition of our invention can contain a vehicle or carrier for the lactone compound. The vehicle can be a liquid such as a non-toxic alcohol, e.g., ethanol, a non-toxic glycol, e.g., propylene glycol, or the like. The carrier can also be an absorbent solid such as a gum (e.g, gum arabic or xanthan gum or guar gum) or components for encapsulating the composition by means of coacervation (such as by gelatin) or by means of formulation of a polymer around a liquid center. This can be accomplished by using a urea formaldehyde prepolymer to form a polymeric capsule around a perfume composition center as is known in the art.

It will be appreciated from the present disclosure that the saturated lactone compounds according to the present invention can be used to alter, vary, fortify, modify, enhance or otherwise improve the flavor of a wide variety of materials which are ingested, consumed or otherwise organoleptically sensed.

The terms "alter" and "modify" in their various forms will be understood herein to mean the supplying or imparting of a flavor character or note to an otherwise bland, relatively tasteless substance, or augmenting an existing flavor characteristic where the natural flavor is deficient in some regard or supplement the existing flavor impression to modify its organoleptic character.

The term "enhance" is intended herein to mean the intensification (by use of the saturated lactone compound of this invention) of a flavor or aroma note or nuance in a foodstuff or perfume composition or perfumed article without changing the quality of said note or nuance.

A "flavoring composition" as referred to herein means one which contributes a part of the overall flavor impression by supplementing or fortifying a natural or artificial flavor in a material or one which supplies substantially all the flavor and/or aroma character to a consumable article.

The term "foodstuff" as used herein included both solid and liquid ingestible material for man or animals which materials usually do, but need not, have nutritional value. Thus, foodstuffs include meats, gravies, soups, convenience foods, malt, alcoholic and other beverages, milk and diary products, seafood, including fish, crustaceans, mollusks and the like, candies, vegetables, cereals, soft drinks, snacks, dog and cat foods, other veterinary products, and the like.

When the saturated lactone compounds of this invention are used in a flavoring composition, they can be combined with conventional flavoring materials or adjuvants.

Such co-ingredients or flavoring adjuvants are well known in the art for such and have been extensively described in the literature. Requirements of such adjuvant materials are : (1) that they be non-reactive with the lactone compound(s) of this invention; (2) that they be organoleptically compatible with the lactone compound(s) of this invention whereby the flavor of the ultimate consumable material to which the lactone compound(s) are added is not detrimentally affected by the use of the adjuvant; (3) that they be ingestible acceptable and thus non-toxic or otherwise non-deleterious. Apart from these requirements, conventional materials can be used and broadly include other flavor materials, vehicles, stabilizers, thickeners, surface active agents, conditioners, and flavor intensifiers.

Such conventional flavoring materials include saturated fatty acids, unsaturated fatty acids and amino acids, alcohols including primary and secondary alcohols, esters, carbonyl compounds including ketones and aldehydes; lactones (other than the lactones of our inventions); other cyclic organic materials including benzene derivatives, alicyclic compounds, heterocyclics such as furans, pyridines, pyrazines and the like; sulfur-containing compounds including thiols, sulfides, disulfides and the like; proteins; lipids, carbohydrates; so-called flavor potentiators such as monosodium glutamate, magnesium glutamate, calcium glutamate, guanylates and inosinates; natural flavoring materials such as cocoa, vanilla and caramel; essential oils and extracts such as anise oil, clove oil, and the like and artificial flavoring materials such as vanillin and the like.

Specific preferred flavor adjuvants are as follows:
anise oil;
ethyl-2-methyl butyrate;
vanillin;
cis-3-heptenol;
cis-3-hexenol;
trans-2-heptenol;
cis-3-heptenal;
butyl valerate;
2,3-diethyl pyrazine;
methyl cyclopentenolone;
benzaldehyde;
valerian oil
3,4-dimethoxyphenol;
amyl acetate;
amyl cinnamate;
gamma butyryl lactone;
furfural;
trimethyl pyrazine;
phenyl acetic acid
isovaleraldehyde;
ethyl maltol;
ethyl vanillin;
ethyl valerate;
cocoa extract;
coffee extract;
peppermint oil;
spearmint oil;
clove oil;
anethol;
cardamom oil;
wintergreen oil;
cinnamic aldehyde;
ethyl-2-methyl valerate;
gamma hexenyl lactone;
2,4-decadienal;
2,4-haptadienal; and
butylidene phthalide.

DETAILED DESCRIPTION OF DRAWINGS

The accompanying GLC profiles illustrate products obtained by carrying out the procedures described in the examples and show slightly different peaks which represent differences in yield.

Figure 1:
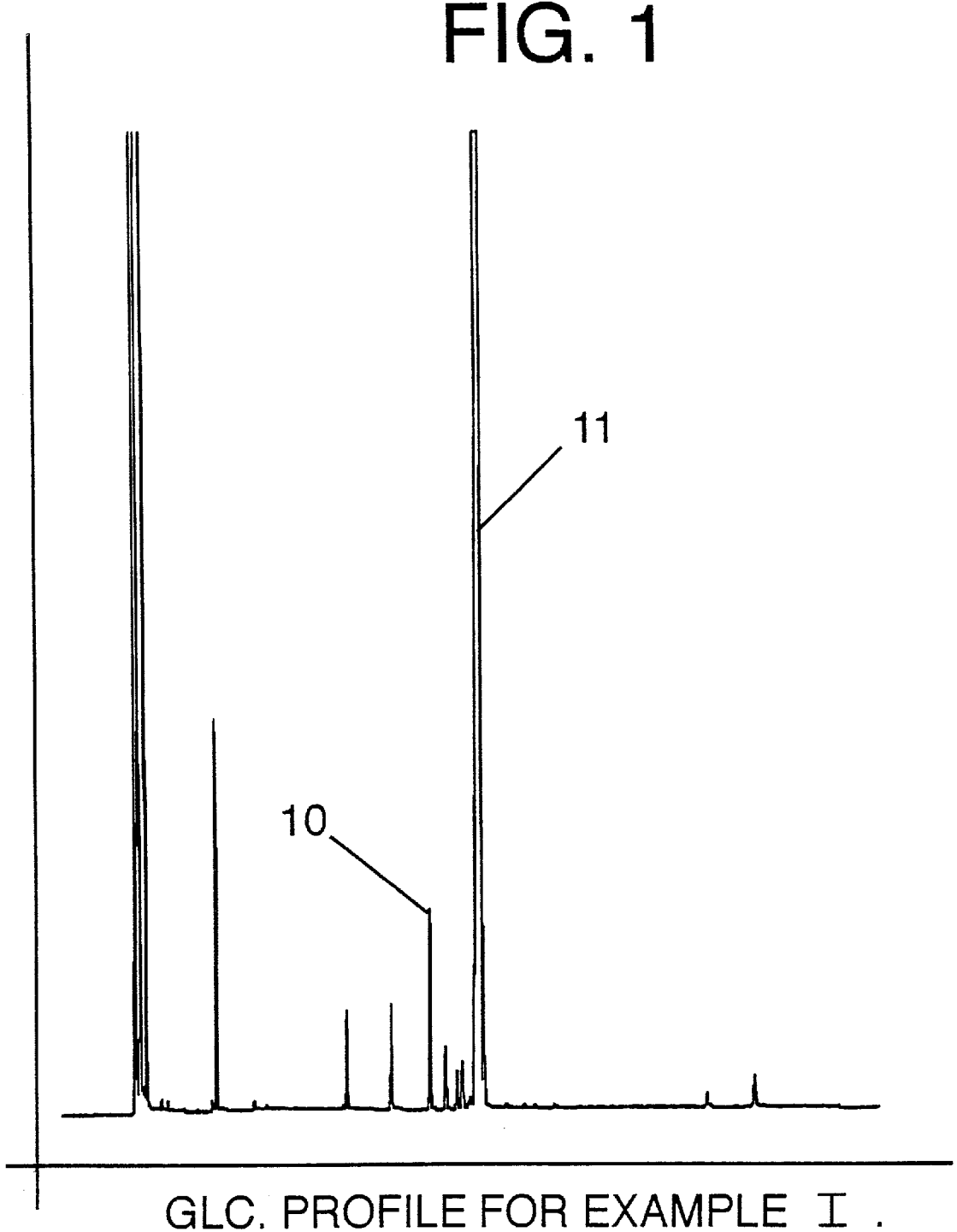
FIG. 1 is a GLC profile of the reaction product for example 1 containing the compound having the structure.

FIG. 1 is a GLC profile for the reaction product of Example 1. The peak indicated by reference numeral 10 is the peak for the compound having the structure:

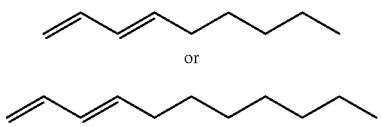

or

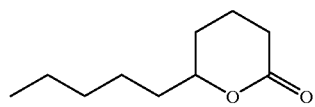

which are impurities in the starting material.

The peak indicated by reference numeral 11 is the peak for the compound having the structure:

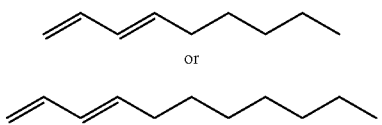

FIG. 2 is a GLC profile for the reaction product of Example 2. The peak indicated by reference numeral 12 is the peak for the compound having the structure: or

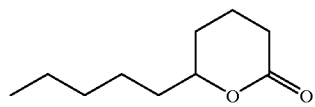

The peak indicated by reference numeral 13 is the peak for the compound having the structure:

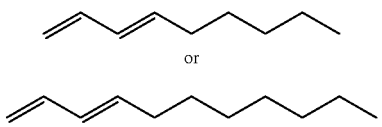

FIG. 3 is the GLC profile for the reaction product of Example 3. The peak indicated by reference number 14 is for the compound having the structure:

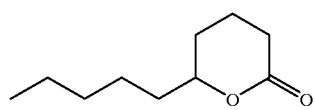

The peak indicated by the reference number 15 is for the compound having the structure:

FIG. 4 is the GLC profile for the reaction product of Example 4. The peak indicated by reference number 16 is for the compound having the structure:

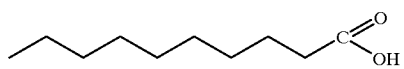

The peak indicated by the reference number 17 is for the compound having the structure: or

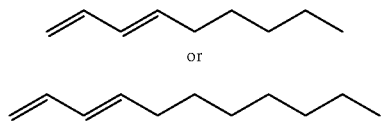

The peak indicated by the reference number 18 is for the compound having the structure:

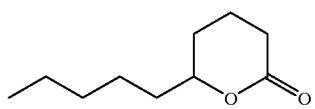

FIG. 5 is a GLC profile for the reaction product of Example 5. The peak indicated by the reference number 19 is for the compound having the structure:

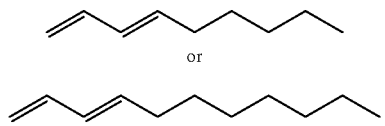

The peak indicated by the reference number 20 is for the compound having the structure:

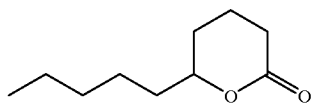

FIG. 6 is the GLC profile for the reaction product of Example 6 using a Massoi $C_{12}$ fraction. The peak indicated by the reference number 21 is for the compound having the structure:

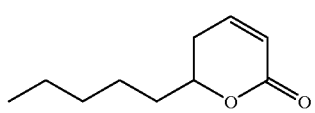

Another of the peaks of FIG. 6 is for the compound having the structure

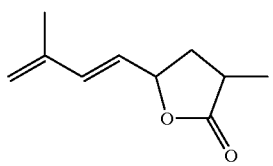

The peak indicated by the reference number 23 is for the compound having the structure:

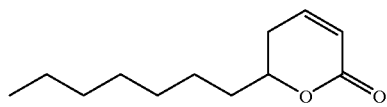

The peak indicated by the reference number 24 is for the compound having the structure:

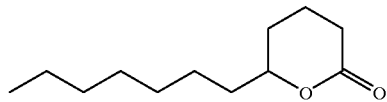

FIG. 7 is the mass spectrum for the Massoi Bark oil starting material used in Example 1. The peak indicated by the reference numeral 25 is for the compound having the structure:

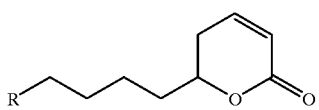

where R=CH$_3$

The peak indicated by the reference number 26 is for the compound having the structure:

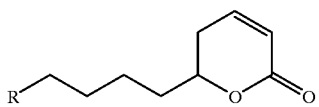

where R=n-propyl

The peak indicated by the reference number 27 is for the compound having the structure:

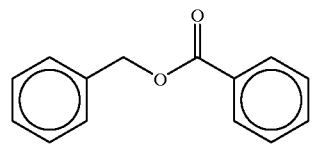

FIG. 8 is the mass spectrum for the Massoi Bark oil starting material used in Example 1. The peak indicated by the reference numeral 28 is for the compound having the structure:

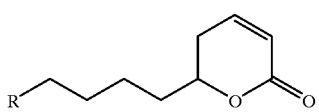

The peak indicated by the reference number 29 is for the compound having the structure:

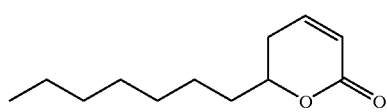

The peak indicated by the reference number 30 is for the compound having the structure:

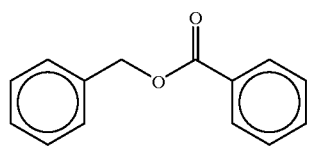

The peak indicated by the reference number 31 is for the compound having the structure:

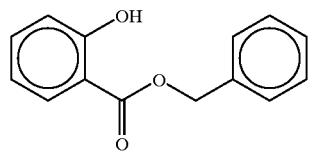

The GC-Mass Spectrum in FIG. 7 was prepared from a methyl silicon column 50 meters in height by 0.32 mm using 0.5 micron bonded fused silica, operated at an initial temperature of 75° C. up to a final temperature of 225° C. at 2° C. per minute for a total time of 30 hours.

The GC-Mass Spectrum column for FIG. 8 is a CARBONWAX 20M column 50 meters ×0.32 mm using 0.3 micron nonbonded fused silica with the temperature of range 75 to 225° C. at a rate 2° C. per minute for a total time of 30 hours.

FIG. 9 is a mass spectrum for the Massoi Bark Oil used in Example 1.

FIG. 10 is a mass spectrum for the starting material Massoi Bark oil. The peak indicated by the reference number 32 is for the compound having the structure:

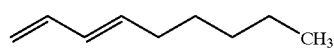

The peak indicated by the reference number 33 is for the compound having the structure:

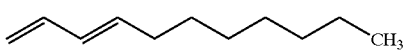

The peak indicated by the reference number 34 is for the compound having the structure:

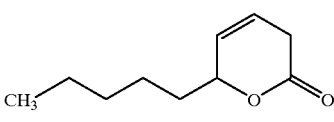

The peak indicated by the reference number 35 is for the compound having the structure:

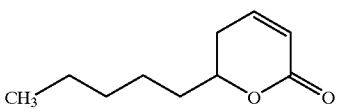

The peak indicated by the reference number 36 is for the compound having the structure:

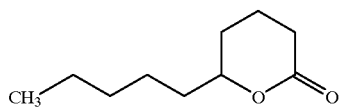

The peak indicated by the reference number 37 is for the compound having the structure:

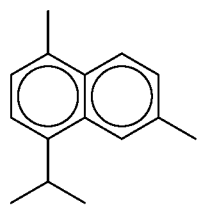

FIG. 11 is a mass spectrum total ion chromatogram (TIC) of the distillation fraction 2 of Example 1. The peak indicated by the reference number 38 is for the compound having the structure:

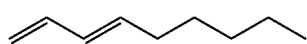

The peak indicated by the reference number 39 is for the compound having the structure:

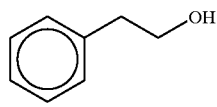

The peak indicated by the reference number 40 is for the compound having the structure:

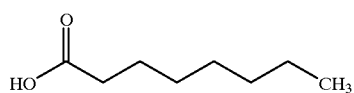

The peak indicated by the reference number 41 is for the compound having the structure:

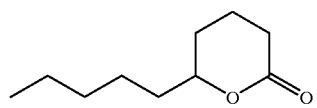

The peak indicated by the reference number 42 is for the compound having the structure:

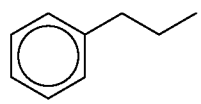

FIG. 11A is an expanded TIC of section A in FIG. 11. The peak indicated by the reference number 43 is for the compound having the structure:

The peak indicated by the reference number 44 is for the compound having the structure:

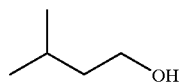

The peak indicated by the reference number 45 is for the compound having the structure:

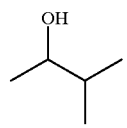

The peak indicated by the reference number 46 is for the compound having the structure:

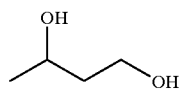

The peak indicated by the reference number 47 is for the compound having the structure:

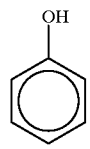

FIG. 11B is an expanded TIC of Section B of FIG. 11. The peak indicated by the reference number 48 is for the compound having the structure:

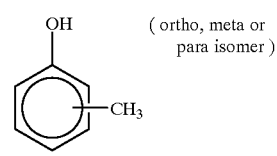

(ortho, meta or para isomer)

The peak indicated by the reference number 49 is for the compound having the structure:

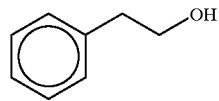
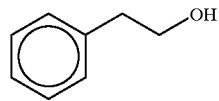

The peak indicated by the reference number 50 is for the compound having the structure:

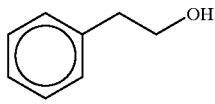

The peak indicated by the reference number 51 is for the compound having the structure:

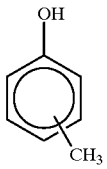

(ortho or para isomer)

FIG. 11C is an expanded TIC of section C of FIG. 11. The peak indicated by the reference number 52 is for the compound having the structure:

The peak indicated by the reference number 53 is for the compound having the structure:

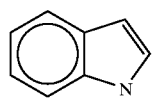

(a mixture wherein in the mixture in each of the compounds one of the dashed lines is a carbon-carbon single bond and the other of the dashed lines is a carbon-carbon go double bond).

The peak indicated by the reference number 54 is for the compound having the structure:

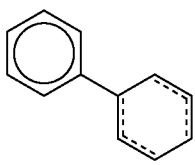

(ortho or para isomer)

The peak indicated by the reference number 55 is for the compound having the structure:

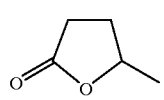

The peak indicated by the reference number 56 is for the compound having the structure:

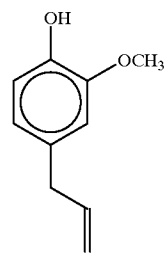

The peak indicated by the reference number 57 is for the compound having the structure:

The peak indicated by the reference number 58 is for the compound having the structure:

The peak indicated by the reference number 59 is for the compound having the structure:

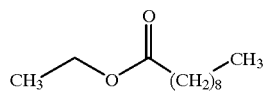

The peak indicated by the reference number 60 is for the compound having the structure:

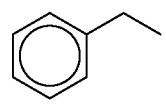

The peak indicated by the reference number 61 is for the compound having the structure:

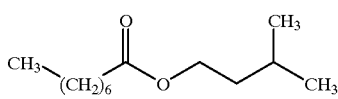

FIG. 11D is an expanded TIC of section D of FIG. 11. The group of peaks indicated by the reference number 62 is for sesquiterpenes.

The peak indicated by the reference number 63 is for the compound having the structure:

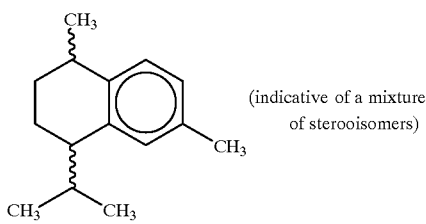
(indicative of a mixture of sterooisomers)

The peak indicated by the reference number 64 is for the compound having the structure:

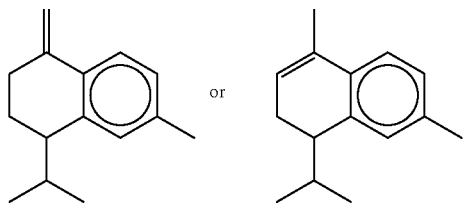

The peak indicated by the reference number 65 is for sesquiterpene alcohol.

The peak indicated by the reference number 66 is for the compound having the structure:

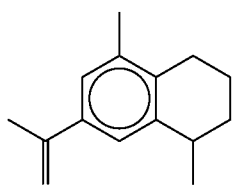

The peak indicated by the reference number 67 is for the compound having the structure:

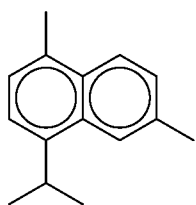

The peak indicated by the reference number 68 is for the compound having the structure:

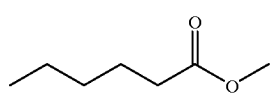

FIG. 12 is a schematic micro representation of the two-phase system of the invention wherein the organic phase indicated by the globules of the substrate-glyceride 69, 69 is admixed with the aqueous nutrient phase 70. The interface 71 is the boundary across which the substrate passes to enter into the controlled oxidative reaction conditions to produce the desired products.

EXAMPLE 1

Using a 35 liter fermenter vessel of conventional configuration the following production medium was prepared in the total amount of 12 liters.

| Ingredient | g/L |
|---|---|
| Glycine | 5.0 |
| $KH_2PO_4$ | 11.0 |
| $MgSO_4$, $7H_2O$ | 3.0 |
| NaCl | 0.1 |
| Yeast Extract | 5.0 |
| Inositol | 0.1 |

A trace metal solution stock was prepared as follows:

| | |
|---|---|
| $FeCl_3$, $6H_2O$ | 45.0 g |
| $CoCl_2$ | 2.0 g |
| $CaCl_2$ | 1.0 g |
| Boric Acid | 0.5 g |
| Sodium Citrate | 73.5 g |
| $ZnCl_2$ | 2.0 g |
| Sodium Molybdate dihydrate | 2.35 g |
| $CuSO_4.5H_2O$ | 3.0 g |
| $MnCl_2$ | 1.6 g |
| deionized water | 1.0 L |

A vitamin solution stock was prepared as follows:

| | |
|---|---|
| Biotin | 0.1 g |
| Folic Acid | 0.1 g |
| Riboflavin | 0.5 g |
| Pyridoxine HCl | 1.40 g |
| Pantothenic Acid | 5.50 g |
| Niacin | 6.10 g |
| 50% NaOH | 5 ml |
| deionized water | 1 L |

The vitamin solution stock and trace metal solution stock were mixed as follows:

| | |
|---|---|
| Vitamin Solution Stock | 5.4 ml |
| Trace metal Solution Stock | 5.4 ml |
| 10% Thimaine HCl | 0.54 ml |
| $CaCl_2.2H_2O$ | 0.2 |

The inoculum used for introduction into the production medium described above was 2% of FERMIPAN® yeast which is a dry Bakers' yeast, Saccharomyces cerevisiae.

The temperature was adjusted to 30° C. and aeration begun to provide 0.42 liters of oxygen per liter of reaction mixture. Agitation was set at 700 rpm.

A mixture was then prepared as the organic phase containing 48 g of 2-decene-1,5-olide(Massoi lactone C10 fraction obtained from the Haldin Company) and 432 grams NEOBEE® oil which is a triglyceride of a C8–C10 fatty acid.

A nutrient feed identified as follows was prepared:

| Ingredient | g/L |
|---|---|
| KH$_2$PO$_4$ | 11.0 |
| MgSO$_4$.7H$_2$O | 3.0 |
| NaCl | 0.2 |
| Yeast Extract | 5.0 |
| Inositol | 0.2 |
| Vitamin Solution | 5.4 ml |
| Trace Metal Solution | 5.4 ml |
| 10% Thiamine HCl | 0.54 ml |
| CaCl$_2$.2H$_2$O | 0.2 ml |

There was sterilized separately 500 grams of corn starch hydrolysate in the form of dextrose identified as CER-ELOSE® 2001 obtained from Corn Products Inc. in Sumit-Argo, Ill.

The pH was maintained automatically at 5.5 with addition of 10% ammonium hydroxide (NH$_4$OH) during fermentation.

In Example 1, the fermenter reactor was inoculated with 2% of the FERMIPANE® yeast which is a dry Saccharomyces cerevisiae yeast also known as Baker's yeast. Nutrient (sugar) feed was commenced at the same time at 60 g/hr. After 7 hours, the dissolved oxygen measured 68.5% and 307 grams of the nutrient feed has been pumped. The solids were determined to be approximately 4.2%. The dissolved oxygen was measured by an oxygen probe.

At seven hours, the Massoi/NEOBEE® oil mixture began pumping into the reactor at a rate of 1.5. g/L/hr. The sugar content measured 0.029 g/L.

After 13 hours the solids measured 10.3% and the dissolved oxygen was determined to be 80.38%. All of the Massoi Oil-NEOBEE® oil mixture was pumped in by that point in time.

After 19 hours the solids content was 9.8% and the dissolved oxygen content 83.8%. At that point 1.669 Kg of the nutrient feed had been pumped in and the sample showed 3.57 g/L of δ-decalactone.

At the end of 31 hours the dissolved oxygen was 80.6%.

At the completion of the reaction at 47 hours the solids were measured at 12% and the dissolved oxygen was determined to be 73.3%. The total nutrient feed that had been pumped in was 2.8 kg.

The crude product was determined to be 35.59 g/L and was then distilled. The distilled product was 6.01 g/L of which 49.1% was the product δ-decalactone (2.95 g/L). FIG. 1 shows the GLC profile of the results of Example 1. The peak indicated by reference numeral 10 represents a compound having the formula:

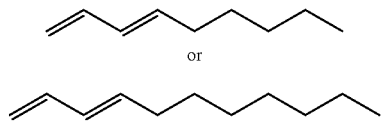

The peak represented by reference numeral 11 represents a compound having the structure:

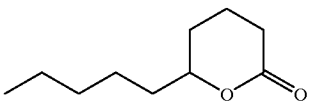

EXAMPLE 2

The fermenter media and nutrient were the same as used in Example 1 except that the inoculation was carried out at 1% concentration of the FERMIPAN® yeast. The nutrient was pumped at a rate of 38.2 g/hr. Six hours after the inoculation the total feed that had been pumped in was 547 grams and the dissolved oxygen was 91% with the solid contents of 7.9%.

Seven hours after commencement of the run, the Massoi/NEOBEE® mixture began pumping into the fermenter reactor at a rate of 29 g/hr. At 21.5 hours the solids measured 9.7% and the dissolved oxygen was 72.4%. The total sugar pumped in at that point was 1.027 kg and the amount of the Massoi substrate that had been pumped in was 120 grams.

At 24 hours, the sugar feeding rate was 82 g/hr.

At 40 hours, the solids content was 8.6% with a dissolved oxygen of 74.4%. The sugar that had been pumped in at that point measured 2.573 kg with the total of the Massoi pumped in at 660.1 grams.

At 45.5 hours the solids were determined at 8.9% with the dissolved oxygen of 88.6% and that the sugar pumped in was 2.863 kg. The total Massoi oil pumped in at that point was 705 grams.

At the completion of the reaction at 60 hours, solids measured at 8.3% with the dissolved oxygen of 94.1%. The sugar pumped in had amounted to 3.523 kg. The crude in the sample was 52.12 g/l. The distillate was 6.95 g/l. The percent product was 68.8% with a total yield of 4.79 g/l of δ-decalactone.

FIG. 2 is the GLC profile of Example 2 and the peak indicated by the reference numeral 12 represents a compound having the structure:

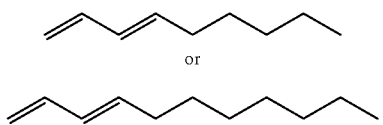

The peak indicated by the reference numeral 13 represents a compound having the structure:

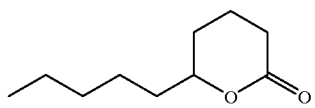

EXAMPLE 3

Example 3 was carried out using the same fermenter media and nutrient feed as in Example 2 except that the mixture of the Massoi lactone C10 fraction of 2-decen-1, 5,-olide was 125 g and the NEOBEE® Oil was 1125 g. The production medium was inoculated with 1% FERMIPAN® yeast to provide a solids content at the start of the reaction of 3.5% with the dissolved 10 air content at 100.%

The sugar feed was introduced at the beginning with a rate of 52.2 g/h.

After 18 hours the mixture of the Massoi oil and the NEOBEE® oil was introduced at the rate of 30 g/h.

After 22.5 hours the solids content rose to 12.1% with the dissolved oxygen of 72.9%. After 24 hours the Massoi/NEOBEE® oil mixture was increased to 50 g/h. and the rpm of the stirrer was increased to 700 due to increased volume. The sugar feed continued pumping at 87.7 g/h. After 41 hours the solids content measured 10.3% with the dissolved oxygen content of 80.4%. The total sugar pumped at this point was determined to be 29.20 kg and the total Massoi Oil pumped in at that point was 1139.6 grams.

After 46.5 hours the solids content was 9.6% and the dissolved oxygen was 85.6%. The sugar pumped up to that point was measured at 3.261 kg and 1200 g of the Massoi oil was pumped in.

At the conclusion of the run at 65 hours the dissolved oxygen measured at 98.7% and the total sugar that had been introduced was 4.025 kg. The crude was determined to be 81.33 g/L with the distillate of 8.11 g/L. The percent product was 90.83% and the recovered amount of δ-decalactone was 7.37 g/L. The total final fermenter volume was 17.25 liters and the total Massoi oil pumped had been 7.25 g/L.

FIG. 3 is a GLC profile of the product obtained from experiment 3. The peak indicated by the reference numeral represents the compound having the structure with the formula:

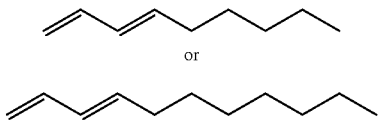

or

The peak represented by the reference numeral 15 represents a compound having the structure:

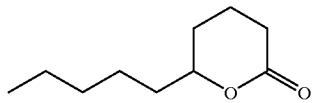

EXAMPLE 4

Using the same procedures, the same production medium and nutrient medium, the production of the saturated δ-decalactone was produced wherein the only difference was that the Massoi oil and the NEOBEE® oil mixture was added all at once 16 hours after the inoculation. At 1½ hour the pumping of the sugar was at the rate of 56 g/h. After 17 hours the solid contents was determined to be 10.3% and the dissolved oxygen was measured by the oxygen probe at 83.7%. At this point, 877 grams of sugar had been pumped which yielded a rate of 0.010 grams per liter of sugar.

At the time the Massoi oil/NEOBEE® oil mixture was added, the sugar pumping was at a rate of 61 grams per hour. At the 20th hour, the dissolved oxygen was determined by the probe at being 81.5%. The sugar concentration was 0.176 grams per liter. The stirring was at a rate of 700 rpm. At 22½ hours the solid contents was determined to be 10.3% and the dissolved oxygen to be 83.7%. The sugar pumped at a rate of 1.25 kg. The rate of sugar was therefore determined to be 0.610 grams per liter. After 25.5 hours, the dissolved oxygen was 90.5% and the sugar feed was pumping at rate 40.6 grams per hour.

At the 41 hour interval, the dissolved oxygen was 106.7% with the solid contents of 8.6%. The sugar pumped so far was 2.035 kg and the rate of sugar addition was 0.642 grams per liter. At 46.5 hours the sugar was determined to be 0.154 grams per liter and was pumping at the rate of 11 grams per hour. At that point, an additional 1% of the FERMIPAN® was added.

At 65 hours the solids content was 11.2% with the dissolved oxygen content of 114%. The sugar was at a level 0.040 grams per liter.

At 70.5 hours the run was terminated and the total kilograms of nutrient feed was measured at 2.256 kg. Of the 125 grams of Massoi lactone added to the fermenter, 115.5 grams had been converted to δ-decalactone for a total percentage of product 84.52 percent. The crude product was determined to 84.13 grams per liter. The distilled product was found to be 8.82 grams per liter to give a product yield of 84.52%.

Therefore 7.45 grams per liter were converted to δ-decalactone.

FIG. 4 is the GLC profile of the product of Example 4. The peak indicated by the reference numeral 16 represents a compound having the structure:

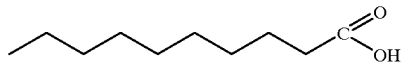

The peak indicated by the reference numeral 17 represents a compound having the structure:

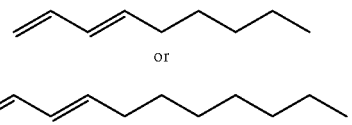

or

The peak represented by the index by the reference numeral 18 represents a compound having the structure:

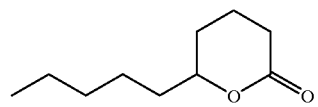

EXAMPLE 5

In Example 5, the run was conducted similar to Example 3 with the following modification.

In this example, the production medium was as follows:
10 g/L KH$_2$PO$_4$
3 g/L MgSO$_4$.7H$_2$O
0.1 g/L NaCl
5 g/L Tastone 900
0.1 g/L Inositol
0.54 ml/L 10% Thiamine HCl solution (32.4 mg/L)
1.35 ml/L 0.04% Biotin solution (0.324 mg/L)
0.2 g/L CaCl$_2$.2H$_2$O The nutrient feed was a 50% solution of the dextrose sold under the brand name CERELOSE® 2001 (O-glucose).

The fermenter was inoculated with 1% FERMIPAN®. After 2 hours, the dissolved oxygen was measured at 80.7 with the sugar pumping at the rate of 62 grams per hour. After 16½ hours, the solids content was indicated as 9.4% with the dissolved air of 65.2%. The sugar content was 0.026 grams per liter and the total sugar pumped up to that time of 946 grams.

After 17 hours, the pumping of the Massoi oil/NEOBEE® oil mixture was commenced at a rate of 50 grams per hour.

At 21½ hours the solids content was determined to be 11.3% and the dissolved oxygen at 56.5%. The total sugar pumped at that point was 1.34 kg with the sugar content of 0.036 grams per liter. At that point the yield of the δ-decalactone was determined to be 0.413 grams per liter. At 24½ hours the dissolved oxygen was 58.4% and the sugar was pumping at a rate of 92 grams per hour.

At 40 hours, the solids content was 8.4% with the dissolved oxygen content of 81.4% and the total amount of sugar pumped at that point was 2.916 kg. It was also determined that there was 4.25 grams per liter of δ-decalactone present.

At 45.5 hours the dissolved oxygen content was 90.7% and the total amount of sugar pumped at that point was 3.444 kg. The sugar content was 0.84 grams per liter and 4.87 grams per liter δ-decalactone were determined.

At the end of the run of 64 hours, a total of 3.84 kg nutrient had been added and the solids content was determined at 8.0% with the dissolved oxygen content of 101.6%. The sugar was determined to be 0.044 grams per liter. The crude product measured 75.87 grams per liter with the distilled decalactone product of 12.69 grams distillate per liter with a purity of 56.3%. It was determined that 117.12 grams was converted to 6- decalactone. A yield of 7.14g/L of lactone with a purity of 99.5% was obtained. A 98% conversion was achieved.

EXAMPLE 6

PREPARATION OF DODECALACTONE

Example 6 was carried out similar to Example 5 with the following modifications. The fermenter reactive volume was six liters of broth in a 14 liter reaction vessel. The substrate material was a 50% the unsaturated compound 2-dodecen-1,5-olide. 30 grams of 2-dodecen-1,5-olide (C 12 fraction) in 200 grams of NEOBEE® oil.

It was determined that after 41 hours, 47% was converted to the δ-dodecalactone product.

After 47 hours, it was determined that 58% had been converted and after the final termination of the run at 60 hours it was determined that 80% of the 2-dodecene-1,5-olide was converted to δ-dodecalactone.

FIG. 6 is a GLC profile of the products produced in Example 6. The peak indicated by the reference numeral 21 represents the compound having the structural formula:

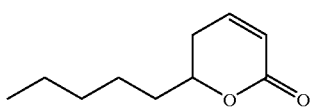

Another peak on the GLC profile of FIG. 6 represents the compound having the structural formula.

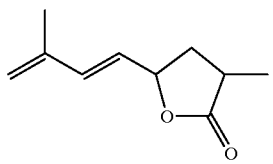

The peak indicated by the reference numeral 23 represents the compound having the structural formula:

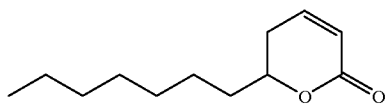

The peak indicated by the reference numberal 24 represents the compound having the structural formula:

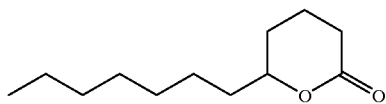

The following examples illustrate the use of the compounds of this invention as components in various compositions to augment or enhance those compositions.

EXAMPLE 7

TABLE I

The following mixture is prepared:

| Ingredients | Parts by Weight | |
|---|---|---|
| | 7A | 7B |
| Orange oil | 50 | 50 |
| Bergamot oil | 20 | 20 |
| Lime oil | 100 | 100 |
| Neroli oil | 5 | 5 |
| 4-(4-methyl-4-hydroxyamyl) delta-cyclohexene carboxaldehyde | 5 | 5 |
| 2.3.3A,4,5,7A-hexahydro--6,7A.8.8-tetramethyl-1.5, methano-1H-inden-1-ol (prepared according to the process of Example 1 of U.S. Pat. No. 3,989,760 | 100 | 100 |
| 1',2',3',4',5',6',7',8',-ocathydro 2',3',8',8'-tetramethyl-2'acetonaphthone isomer mixture produced according to the process of Example VII U.S. Pat. No. 3,911,018 | 50 | 50 |
| Gamma methyl ionone | 20 | 20 |
| 1-acetyl-2,5,5,-trimethylcycloheptane produced according to U.S. Pat. No. 3,869,411 | 50 | 50 |
| Compound prepared according to Example 1 | 150 | 0 |
| Compound prepared according to Example 6 | 0 | 150 |

The lactone prepared according to Example 1 adds to this pactchouli formulation a sophisticated, intense, substantive, peach-like aroma profile with sweet, creamy and nut-like topnotes and heavy fruity undertones.

The compound of Example 6 adds to this patchouli formulation a fresh, fruity, aroma with peach undertones.

EXAMPLE 8

PREPARATION OF SOAP COMPOSITIONS

One hundred grams of soap chips are produced according to Example V of U.S. Pat. No. 4,058,487, the specification for which is incorporated herein by reference as follows:

The sodium salt of an equal mixture of $C_{10}$–$C_{14}$ alkane sulfonate (95% active), 40 pounds, is dissolved in a mixture of 80 pounds of anhydrous isopropanol and 125 pounds of deionized water at 150° F. In this mixture is dissolved 10 pounds of partially hydrogenated coconut oil fatty acids and 15 pounds of sodium mono-$C_{14}$ alkyl maleate, and the pH of this solution is adjusted to 6.0 by the addition of a small amount of 50% aqueous solution of sodium hydroxide. The isopropanol is distilled off and the remaining aqueous solution is drum dried. The resulting solid actives are then blended in a chip mixture with 10 pounds of water, 0.2 pounds of titanium hydroxide and 0.7 pounds of one of the perfume ingredients set forth in Table II below. The chips are then plodded into logs, cut to size and finally stamped into bars having a pH of approximately 6.9.

Each of the perfumed soaps produced by means of the foregoing procedure manifests an excellent aroma as set forth in Table II, infra:

TABLE II

| Ingredient | Fragrance Profile |
| --- | --- |
| Compound produced according to Example 1 | a peach aroma with sweet, creamy, nut-like topnotes and heavy fruity undertones |
| Compound prepared according to Example 6 | a fresh, fruity aroma with peach undertones |
| Perfume composition of Example 7A | a patchouli aroma with heavy fruity, peach-like undertones and sweet, creamy and nut-like topnotes |
| Perfume composition of Example 7B | a patchouli aroma with fresh, fruity, pear undertones |

EXAMPLE 9

PREPARATION OF A DETERGENT COMPOSITION

A total of 100 grams of a detergent powder prepared according to U.S. Pat. No. 4,058,472 (the specification for which is incorporated by reference herein) and containing 5% by $C_{14}$–$C_{18}$ alkyl catechol as a surface active component, the mixture being 60 parts by weight of mono-$C_{14}$–$C_{18}$ alkyl catechol, 35% sodium tetrapyrophosphate, 30% sodium silicate, 20% of sodium carbonate, 3% of sodium carboxymethyl cellulose and 7% of starch is mixed with 0.15 grams individually with each of the aroma ingredients set forth in Table II of Example 8 until a substantially homogeneous composition is obtained. Each of the compositions has an excellent aroma as set forth in Table II of Example 8.

EXAMPLE 10

PREPARATION OF A COSMETIC POWDER COMPOSITION

A cosmetic powder is prepared by mixing in a ball mill, 100 grams of talcum powder with 0.25 grams of each of the perfume materials of Table II of Example 8. Each of the powders has an excellent aroma as set forth in Table II of Example 8.

EXAMPLE 11

PERFUMED LIQUID DETERGENT

Concentrated liquid detergents with aromas as set forth in Table II of Example 8 are prepared by adding 0.10%, 0.151 and 0.20% of each of the ingredients set forth in Table II of Example 8. They are prepared by adding and homogeneously mixing the appropriate quantity of perfume substance of Table II of Example 8 in the liquid detergent. The detergents individually possess aromas as set forth in Table II of Example 8, the intensity increasing with greater concentration of perfume substances set forth in Table II of Example 8.

EXAMPLE 12

PREPARATION OF A COLOGNE HANDKERCHIEF-PERFUME

Each of the ingredients of Table II of Example 8 is incorporated individually into colognes of several strengths at concentrations of 2.0%, 2.5%, 3.0%, 3.5%, 4.0% and 5.0% in 75%, 80%, 85%, 90% and 95% aqueous ethanol; and into several concentrations of handkerchief perfumes at the rate of 15%, 20% and 25% (in 80%, 85%, 90% and 95% aqueous ethanol). Distinct and definite aromas as set forth in Table II of Example 8 are imparted to the colognes and to the handkerchief perfumes at the several concentrations set forth above.

EXAMPLE 11

PREPARATION OF SOAP COMPOSITIONS

One hundred grams of soap chips (IVORY® produced by the Proctor & Gamble Company of Cincinnati, Ohio) are admixed with one gram of each of the substances set forth in Table II of Example 8, supra, until homogenous compositions are obtained. In each of the cases, the homogeneous compositions are heated under 3 atmospheres pressure at 180° C. for a period of three hours and the resulting liquids are placed into soap molds. The resulting soap cakes, on cooling, manifest excellent aromas as set forth in Table II of Example 8.

EXAMPLE 12

PREPARATION OF SOLID DETERGENT COMPOSITIONS

Detergents are prepared from the following ingredients according to Example I of Canadian-Patent No. 1,007,948, the specification for which is incorporated by reference herein:

| Ingredients | Parts by weight |
| --- | --- |
| NEODOL ® 45–11 (a $C_{14}$–$C_{15}$ alcohol ethoxylated with 11 moles of ethylene oxide | 12 |
| Sodium carbonate | 55 |
| Sodium citrate | 20 |
| Sodium sulfate, water brighteners | q. s. |

The detergent is a "phosphate-free" detergent. A total of 100 grams of said detergent is admixed with 0.10, 0.15, 0.20 and 0.25 grams of each of the substances set forth in Table II of Example 8, supra. Each of the detergent samples has an excellent aroma as indicated in Table II of Example 8.

EXAMPLE 13

PREPARATION OF DRIER-ADDED FABRIC SOFTENER ARTICLE

Utilizing the procedure of Example I at column 15 of U.S. Pat. No. 3,632,396 the specification for which is incorporated by reference herein, a non-woven cloth substrate useful as a drier-added fabric softening article of manufacture is prepared wherein the substrate, substrate coating and outer coating and the perfume material are as follows:

1. a water "dissolvable" paper ("Dissolve Paper") as the substrate.

2. ADOGEN®448 (melting point about 140° F.) as the first substrate coating; and 3. an outer coating having the following formulation (melting point about 150° F.):

57% $C_{20}$–$C_{22}$ HAPS;

22% isopropyl alcohol;

20% antistatic agent 1% of one of the perfumery substances set forth in Table II of Example 8, supra.

Fabric softening compositions containing the substances as set forth in Table II of Example 8, supra, essentially consist of a substrate having a weight of about 3 grams per 100 square inches; a substrate coating weighing about 1.85 grams per 100 square inches of substrate; and an outer coating weighing about 1.5 grams per 100 square inches of substrate are prepared thereby providing a total aromatized substrate and outer coating weight ratio of about 1:1 by weight of the substrate.

The aromas as set forth in Table II of Example 8, supra, are imparted in a pleasant manner to the head space in a drier on operation thereof using the said drier-added fabric softening non-woven fabric by adding to the drying cycle.

As stated above in the case of fabric softener articles, the entire U.S. Pat. No. 3,632,396 is incorporated by reference herein. Thus, all of the articles of U.S. Pat. No. 3,632,396 acting as fabric softening articles in said U.S. Patent may be perfumed in their outer coating with from 0.25% up to 5% by weight of each of the perfuming substances of Table II of Example 8, supra.

EXAMPLE 14

HAIR PREPARATION

A "soft-feel, good-hold" hair spray is produced containing the following ingredients:

| Ingredients | Parts by Weight |
| --- | --- |
| Polyvinylpyrollidone/vinyl acetate "E-735 Copolymer" manufactured by the GAF Corporation of New York, NY | 4.00 |
| Anhydrous ethanol | 70.90 |
| Dioctyl sebecate | 0.05 |
| Benzyl alcohol | 0.05 |
| "Propellant A46" manufactured by the GAF Corporation of New York, NY | 24.95 |
| Fragrance ingredient as set forth in Table II of Example 8, supra. | 0.05 |

The PVP/VA copolymers are first dissolved in alcohol and all other ingredients are added until uniform. The propellant is then pressurized and used as an aerosol. The resulting hair sprays each have pleasant aromas as set forth in Table II of Example 8.

EXAMPLE 15

SCOURING CLEANSER COMPOSITION

A scouring cleanser composition is prepared in accordance with Example I at columns 11 and 12 of U.S. Pat. No. 4,193,888 issued on Mar. 18, 1980, the specification for which is incorporated by reference herein. To this composition, the substances set forth in Table II of Example 8, supra, are added at the level of 025% as set forth in the table in said Example I of U.S. Pat. No. 4,193,888 yielding an aroma on using said cleanser in ordinary circumstances which is quite pleasant and described in Table II of Example 8, supra.

EXAMPLE 16

A fabric softening article prepared substantially as set forth in Example VII of Canadian Patent No. 1,069,260, the specification for which is incorporated by reference herein, is prepared containing 0.21% by weight of a perfuming substance as set forth in Table II of Example 8, supra, and yielding one use in a drier, a faint aroma as set forth in Table II of Example 8, supra.

EXAMPLE 17

PUDDING

At the rate of 0.8 ppm (i) the lactone produced according to Example 1 and (ii) the lactone produced according to Example 6 are separately added to a ROYAL® BUTTERSCOTCH PUDDING pudding.

When the lactone of Example 1 is added, pleasant aesthetically pleasing, pear, plum-like, buttery and peach nuances were added to the butterscotch pudding with the panel of 30 members preferring the butterscotch pudding with the lactone added thereto to a butterscotch pudding without the lactone of Example 1 added thereto.

When the lactone of Example 6 is added, pleasant aesthetically pleasing, peach, coconut, and creamy nuances were added to the butterscotch pudding with the panel of 30 members preferring the butterscotch pudding with the lactone of Example 6 added thereto to a butterscotch pudding without the lactone added thereto.

EXAMPLE 18

FLAVOR FORMULATIONS

The following natural rich orange formulations are prepared:

| | Parts by Weight | |
|---|---|---|
| Ingredient | 18A | 18B |
| Compound defined according to the structure: | 26.0 | 26.0 |

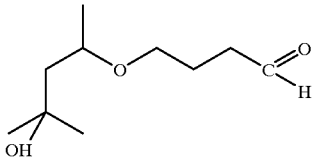

| | | |
|---|---|---|
| prepared according to Example VI of U.S. Pat. No. 4,532,364. | | |
| The lactone produced according to Example 1 | 12.00 | 0 |
| The lactone produced according to Example 6 | 0 | 12 |
| Natural Lemon Oil Terpeneless | 10.0 | 10.0 |
| Acetaldehyde | 0.6 | 0.6 |
| Alpha-terpineol | 2.1 | 2.1 |
| Citral | 1.8 | 1.8 |
| Carvone | 0.24 | 0.24 |
| Terpinolene | 1.2 | 1.2 |
| Alpha-terpinene | 0.25 | 0.25 |
| Diphenyl | 0.25 | 0.25 |
| Alpha-Fenchyl Alcohol | 0.25 | 0.25 |
| Limonene | 0.35 | 0.35 |
| Linalool | 0.25 | 0.25 |
| Gereanyl Acetate | 0.25 | 0.25 |
| Nootkatone | 0.25 | 0.25 |
| Neryl Acetate | 0.25 | 0.25 |

A third flavor formulation is prepared which is identical to the above formulations, except without the lactones of Example 1 or Example 6.

The flavor formulation of Example 18A with the lactone of Example 1 has a definite natural rich orange aroma and taste with pear, plum-like, peach and buttery nuances due to the addition of the pear, plum-like, peach and buttery principals to this citrus flavor.

The flavor formulation of Example 18B with the lactone of Example 6 has a definite rich orange aroma and taste with peach, coconut and creamy nuances due to the addition of peach, coconut, and creamy principals to this citrus flavor.

The lactones of Examples 1 and 6 added thereto are used in the following examples.

EXAMPLE 19

A. POWDER FLAVOR COMPOSITIONS

20 Grams of the flavor compositions of Examples 18A and 18B containing the lactones of Examples 1 and 6 are emulsified in a solution containing 300 grams gum acacia and 700 grams water. The emulsions are spray-dried with a Bowen Lab Model Drier utilizing 260 c.f.m. of air with an inlet temperature of 500° F., an outlet temperature of 200° F., and a wheel speed of 50,000 rpm.

B. SUSTAINED RELEASE FLAVOR

| Ingredients | Parts by Weight |
|---|---|
| Liquid Citrus Flavor Compositions of Example 18A and 18B (separately) | 20.0 |
| Propylene glycol | 9.0 |
| CAB-O-SIL ® M-5 (Brand of Silica produced by the Coat Corporation of 125 High Street Boston, MA 0210): | 5.00 |

Physical Properties:
Surface area: 200 m$_2$/gm
Nominal particle size: 0.012 microns
Density: 2.3 lbs/cu. ft.)

The CAB-O-SIL® is dispersed in the liquid citrus flavor compositions of Example 18A and 18B with vigorous stirring, thereby resulting in each case in a viscous liquid. 71 Parts by weight of the powder flavor compositions of Part "A", supra, are then separately blended into the said viscous liquids, with stirring, at 25° C. for a period of 30 minutes resulting in dry, free flowing sustained release flavor powder.

EXAMPLE 20

10Parts by weight of 50 Bloom pigskin gelatin is added to 90 parts by weight of water at a temperature of 150° F. The mixture is agitated until the gelatin is completely dissolved and the solution is cooled to 120° F. Separately, 20 parts by weight of the liquid flavor compositions of Examples 18A and 18B are added to the solution which is then homogenized to form an emulsion having particle size typically in the range of 5–40 microns. This material is kept at 120° F. under which conditions the gelatin will not jell.

Coacervation is induced by adding, slowly and uniformly 40 parts by weight of a 20% aqueous solution of sodium sulphate. During coacervation the gelatin molecules are deposited uniformly about each oil droplet as a nucleus.

Gelation is effected by pouring the heated coacervate mixtures into 1,000 parts by weight (each) of 7% aqueous solutions of sodium sulphate at 65° C. The resulting jelled coacervates may be filtered and washed with water at temperatures below the melting point of gelatin, to remove the salt.

Hardening of the filtered cake, in this example, is effected by washing with 200 parts by weight of 37% solution of formaldehyde in water. The cake is then washed to remove residual formaldehyde.

EXAMPLE 21

CHEWING GUM

100 Parts by weight of chicle are mixed with 4 parts by weight of each of the two flavors prepared in accordance with Example 19B. 300 Parts of sucrose and 100 parts of corn syrup are added. Mixing is effected in a ribbon blender with jacketed side walls of the type manufactured by the Baker Perkins Company.

The resultant chewing gum blends are then each manufactured into strips 1 inch in width and 0.1 inches in thickness. The strips are cut into lengths of 3 inches each. On chewing, each of the chewing gum has a pleasant, long-lasting rich citrus flavor.

EXAMPLE 22

CHEWING GUM

100 Parts by weight of chicle are mixed with 18 parts by weight of each of the flavors prepared in accordance with Example 19B. 300 Parts of sucrose and 100 parts of corn syrup are then added. Mixing is effected in a ribbon blender with jacketed side walls of the type manufactured by the Baker Perkins Company.

The resultant chewing gum blends are then manufactured into strips 1 inch in width and 0.1 inches in thickness. The strips are cut into lengths of 3 inches each. On chewing each of, the chewing gums has a pleasant, long-lasting rich citrus flavor.

EXAMPLE 23

TOOTHPASTE FORMULATION

The following separate groups of ingredients are prepared:

| Parts by Weight | Ingredients |
|---|---|
| Group "A" | |
| 30.200 | Glycerine |
| 15.325 | Distilled Water |
| .100 | Sodium Benzoate |
| .125 | Saccharin Sodium |
| .400 | Stannous Fluoride |
| Group "B" | |
| 12.500 | Calcium carbonate |
| 37.200 | Dicalcium Phosphate (Dihydrate) |
| Group "C" | |
| 2.000 | Sodium N-Lauroyl Sarcosinate (foaming agent) |
| Group "D" | |
| 1.200 | Flavor Materials of Example 19B |

1. The ingredients in Group "A" are stirred and heated in a steam jacketed kettle to 160° F.;
2. Stirring is continued for an additional three to five minutes to form a homogeneous gel;
3. The powders of Group "B" are added to the gel, while mixing, until a homogeneous paste is formed;
4. With stirring, one of the flavors "D" is added and lastly the sodium n-lauroyl sarcosinate;
5. The resultant slurry is then blended for one hour. The completed paste is then transferred to a three roller mill and then homogenized, and finally tubed.

The resulting toothpastes when used in normal toothbrushing procedures yield pleasant rich citrus flavors, of constant strong intensity throughout said procedure (1–1.5 minutes).

EXAMPLE 24

CHEWABLE VITAMIN TABLETS

The flavor materials produced according to the process of Example 19B are each added to a Chewable Vitamin Tablet Formulation at a rate of 10 gm/Kg which chewable vitamin tablet formulation is prepared as follows:

In a Hobart Mixer the following materials are blended to homogeneity:

| | Gms/1000 Tablets |
|---|---|
| Vitamin C (ascorbic acid) as ascorbic acid-sodium ascorbate mixture 1:1 | 70.0 |
| Vitamin B$_1$ (thiamine mononitrate) as | 4.0 |
| ROCOAT ® thiamine mononitrate 33 ⅓ (Hoffman La Roche) | |
| Vitamin B$_2$ (riboflavin) as ROCOAT ® riboflavin 33 ⅓% | 5.0 |
| Vitamin B$_6$ (pyridoxine hydrochloride) as ROCOAT ® pyridoxine hydrochloride 33 ⅓% | 4.0 |
| Niacinamide as ROCOAT ® niacinamide 33 ⅓% | 33.0 |
| Calcium pantothenate | 11.5 |
| Vitamin B$_{12}$ (cyanocobalamin) (Merck) 0.1% in gelatin | 3.5 |
| Vitamin E (dl-alpha tocopheryl acetate) as dry Vitamin E acetate 33 ⅓% Roche | 6.6 |
| d-Biotin | 0.004 |
| One of the Flavors of Example 19 B | (as indicated above) |
| Certified lake color | 5.0 |
| Sweetener - sodium saccharin | 1.0 |
| Magnesium stearate lubricant | 10.0 |
| Mannitol | (q.s. to make) 500.0 |

Preliminary tablets are prepared by slugging with flat-faced punches and grinding the slugs to 14 mesh. 13.6 G dry Vitamin A Acetate and 0.6 g Vitamin D are then added as beadlets. The entire blend is then compressed using concave punches at 0.5 g each.

Chewing of the resultant tablets yields pleasant, long-lasting, consistently strong rich citrus flavors for a period of 12 minutes.

EXAMPLE 25

To 100 parts by weight of GOYAO mango nectar (produced by the Goya Corporation of New York, N.Y.) is added 10 ppm of the lactone produced according to Example 1. The lactone mixture adds to the mango nectar a very natural nuance which although present in natural mango (prior to adding the lactone of Example 1) lost in the canning process when the mango nectar is prepared and canned in the usual manner.

We claim:

1. A process for the production of a δ-lactone compound represented by the structural formula:

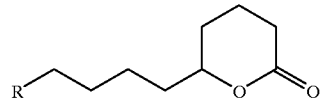

wherein R is a member selected from the group consisting of methyl and n-propyl comprising:
 (a) preparing an aqueous nutrient medium containing a nutrient source, a buffer and yeast extract at a pH in the range of from about 3.5 up to about 8.0;
 (b) preparing as a Saccharomyces yeast culture suspension by inoculating a medium comprising water, a carbon source, a nitrogen source and one or more inorganic salts with a Saccharomyces yeast;
 (c) mixing the resulting yeast culture suspension with the aqueous nutrient medium in order to form a first aqueous liquid phase
 (d) preparing as a second organic liquid phase an admixture of:
  (i) an organic phase former which is a triglyceride of a fatty acid or high molecular weight hydrocarbon; and (ii) a natural 2-decen-1,5-olide or a natural 2-dodecen-1,5-olide represented by the structural formula:

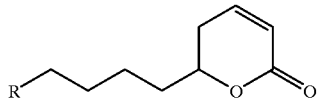

wherein R is selected from the group consisting of methyl and n-propyl;

(e) mixing said first aqueous liquid phase and said second organic liquid phase together with agitation in order to form a reaction medium;

(f) feeding dextrose to said reaction medium at a rate of 5 to 72 g/L/hr so as to maintain said dextrose at a concentration of from 0.01 up to 1.5 grams/liter; and (g) supplying the reaction medium with an oxygen-containing gas at such a rate as to enable the oxygen level in the reaction medium to be maintained at a level of at least about 0.1 liters/liter of reaction mixture; whereby at least 10% dissolved oxygen as measured by a standard oxygen probe is present in the reaction medium at all times during the reaction, in order to maintain oxidative growth conditions to thereby achieve a biotransformation in the presence of a yeast capable of producing said natural δ-lactone compound having the structure:

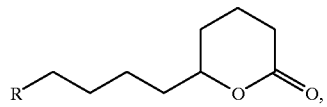

the biotransformation being carried out at a temperature in the range of from 20–50° C.

2. The process according to claim 1 wherein the dextrose concentration in the reaction medium is maintained at from 0.03 up to 0.07 g/L.

3. The process according to claim 1 wherein said fatty acid is a $C_8$–$C_{10}$ fatty acid.

4. The process according to claim 1 wherein said nutrient medium is fed into said reaction medium at a rate sufficient to enable said yeast to maintain oxidative growth and thereby generate said lactone compound defined according to the structure:

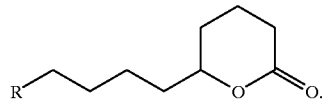

5. The process according to claim 1 wherein the aeration is delivered at a rate enabling interaction with said source of dextrose to avoid production of unwanted alcohol.

6. The process according to claim 1 comprising the additional steps of (h) isolating a lactone-rich composition from the organic phase; and (i) separating the organic phase from the second aqueous phase after carrying out the reaction for a period of from about 2 hours up to about 240 hours.

7. The process according to claim 1 wherein the Saccharomyces yeast is *Saccharomyces cerevisiae*.

8. A composition produced by the process according to claim 6 wherein R is methyl and having a GLC profile corresponding to FIG. 1.

9. A composition produced by the process according to claim 6 wherein R is methyl and having a GLC profile corresponding to FIG. 2.

10. A composition produced by the process according to claim 6 wherein R is methyl and having a GLC profile corresponding to FIG. 3.

11. A composition produced by the process according to claim 6 wherein R is methyl and having a GLC profile corresponding to FIG. 4.

12. A composition produced by the process according to claim 6 wherein R is methyl and having a GLC profile corresponding to FIG. 5.

13. A composition produced by the process according to claim 6 wherein R is n-propyl and having a GLC profile corresponding to FIG. 6.

14. A foodstuff composition consisting essentially of a foodstuff base and intimately admixed therein a flavor augmenting, enhancing or imparting quantity and concentration of the composition defined according to claim 8.

15. A foodstuff composition consisting essentially of a foodstuff base and intimately admixed therein a flavor augmenting, enhancing or imparting quantity and concentration of the composition defined according to claim 9.

16. A foodstuff composition consisting essentially of a foodstuff base and intimately admixed therein a flavor augmenting, enhancing or imparting quantity and concentration of the composition defined according to claim 10.

17. A foodstuff composition consisting essentially of a foodstuff base and intimately admixed therein a flavor augmenting, enhancing or imparting quantity and concentration of the composition defined according to claim 11.

18. A foodstuff composition consisting essentially of a foodstuff base and intimately admixed therein a flavor augmenting, enhancing or imparting quantity and concentration of the composition defined according to claim 12.

19. A foodstuff composition consisting essentially of a foodstuff base and intimately admixed therein a flavor augmenting, enhancing or imparting quantity and concentration of the composition defined according to claim 13.

20. A process for augmenting, enhancing or imparting an aroma or taste in or to a consumable material selected from the group consisting of foodstuffs and chewing gums intimately admixing an aroma and taste augmenting, enhancing or imparting amount and concentration of the composition defined according to claim 7 with a consumable material base.

* * * * *